US012678191B2

(12) United States Patent
Thai et al.

(10) Patent No.: US 12,678,191 B2
(45) Date of Patent: Jul. 14, 2026

(54) ANCHOR FOR TRANSCATHETER ACCESS INTO THE CORONARY SINUS

(71) Applicant: Edwards Lifesciences Corporation, Irvine, CA (US)

(72) Inventors: Linda Thai, Mission Viejo, CA (US); Michael G. Valdez, Riverside, CA (US); Tarannum Ishaq Gutierrez, Ladera Ranch, CA (US); Don Huy Tran, Westminster, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 1145 days.

(21) Appl. No.: 17/507,734

(22) Filed: Oct. 21, 2021

(65) Prior Publication Data

US 2022/0039833 A1 Feb. 10, 2022

Related U.S. Application Data

(63) Continuation of application No. PCT/US2020/027147, filed on Apr. 8, 2020.

(Continued)

(51) Int. Cl.
*A61M 25/01* (2006.01)
*A61B 17/34* (2006.01)
(Continued)

(52) U.S. Cl.
CPC ...... *A61B 17/3423* (2013.01); *A61B 17/3468* (2013.01); *A61B 2017/00243* (2013.01);
(Continued)

(58) Field of Classification Search
CPC ............ A61B 17/3423; A61B 17/3468; A61B 2017/00243; A61B 2017/00292;
(Continued)

(56) References Cited

U.S. PATENT DOCUMENTS 3,538,917 A 11/1970 Selker
3,675,656 A 7/1972 Hakim
(Continued)

FOREIGN PATENT DOCUMENTS

WO 2020215090 A1 10/2020
WO 2021091566 A1 5/2021
(Continued)

OTHER PUBLICATIONS

Menasche, et al. Retrograde Cardioplegia Through the Coronary Sinus, Ann Thorac Surg 44.214-216, Aug. 1987 (Year: 1987).*
(Continued)

*Primary Examiner* — Katherine M Rodjom
(74) *Attorney, Agent, or Firm* — Chang and Hale LLP

(57) ABSTRACT

A delivery sheath can comprise an elongate tubular member and an anchor on a distal portion of the elongate tubular member, the anchor being configured to engage with the coronary sinus ostium, or both the coronary sinus ostium and a portion of the coronary sinus adjacent to the ostium, so as to provide stable transcatheter access into the coronary sinus. The anchor can be configured to permit blood flow through the ostium while in engagement with the ostium.

20 Claims, 14 Drawing Sheets

Related U.S. Application Data

(60) Provisional application No. 62/836,851, filed on Apr. 22, 2019.

(51) Int. Cl.
    *A61B 17/00*     (2006.01)
    *A61M 25/10*     (2013.01)

(52) U.S. Cl.
    CPC .............. *A61B 2017/00292* (2013.01); *A61B 2017/3425* (2013.01); *A61B 2017/3486* (2013.01); *A61M 25/1002* (2013.01)

(58) Field of Classification Search
    CPC ...... A61B 2017/3486; A61M 25/1002; A61M 2025/1086; A61F 2/2451
    See application file for complete search history.

(56) References Cited

U.S. PATENT DOCUMENTS

| | | |
|---|---|---|
| 3,730,186 A | 5/1973 | Edmunds, Jr. et al. |
| 3,853,126 A | 12/1974 | Schulte |
| 3,882,862 A | 5/1975 | Berend |
| 3,882,882 A | 5/1975 | Preisig |
| 3,903,894 A | 9/1975 | Rosen et al. |
| 4,256,094 A | 3/1981 | Kapp et al. |
| 4,428,365 A | 1/1984 | Hakky |
| 4,556,050 A | 12/1985 | Hodgson et al. |
| 4,578,061 A | 3/1986 | Lemelson |
| 4,586,501 A | 5/1986 | Claracq |
| 4,601,718 A | 7/1986 | Possis et al. |
| 4,655,777 A | 4/1987 | Dunn et al. |
| 4,708,140 A | 11/1987 | Baron |
| 4,712,551 A | 12/1987 | Rayhanabad |
| 4,739,762 A | 4/1988 | Palmaz |
| 4,762,128 A | 8/1988 | Rosenbluth |
| 4,774,949 A | 10/1988 | Fogarty |
| 4,828,544 A | 5/1989 | Lane et al. |
| 4,861,336 A | 8/1989 | Helzel |
| 4,881,939 A | 11/1989 | Newman |
| 4,946,457 A | 8/1990 | Elliott |
| 4,950,227 A | 8/1990 | Savin et al. |
| 4,961,729 A | 10/1990 | Vaillancourt |
| 4,997,431 A | 3/1991 | Isner et al. |
| 5,026,377 A | 6/1991 | Burton et al. |
| 5,054,492 A | 10/1991 | Scribner et al. |
| 5,108,420 A | 4/1992 | Marks |
| 5,109,420 A | 4/1992 | Nonaka |
| 5,167,239 A | 12/1992 | Cohen et al. |
| 5,190,528 A | 3/1993 | Fonger et al. |
| 5,193,546 A | 3/1993 | Shaknovich |
| 5,201,757 A | 4/1993 | Heyn et al. |
| 5,242,397 A | 9/1993 | Barath et al. |
| 5,242,410 A | 9/1993 | Melker |
| 5,258,042 A | 11/1993 | Mehta |
| 5,267,940 A | 12/1993 | Moulder |
| 5,287,861 A | 2/1994 | Wilk |
| 5,295,959 A * | 3/1994 | Gurbel .............. A61M 25/1002 |
| | | 604/103.1 |
| 5,330,496 A | 7/1994 | Alferness |
| 5,334,217 A | 8/1994 | Das |
| 5,345,940 A | 9/1994 | Seward et al. |
| 5,354,279 A | 10/1994 | Hofling |
| 5,366,490 A | 11/1994 | Edwards et al. |
| 5,373,849 A | 12/1994 | Maroney et al. |
| 5,395,331 A | 3/1995 | O'Neill et al. |
| 5,419,777 A | 5/1995 | Hofling |
| 5,423,878 A | 6/1995 | Franz |
| 5,429,634 A | 7/1995 | Narciso, Jr. |
| 5,431,700 A | 7/1995 | Sloan |
| 5,443,497 A | 8/1995 | Venbrux |
| 5,445,600 A | 8/1995 | Abdulla |
| 5,445,646 A | 8/1995 | Euteneuer et al. |
| 5,456,284 A | 10/1995 | Ryan et al. |
| 5,456,712 A | 10/1995 | Maginot |
| 5,462,523 A | 10/1995 | Samson et al. |
| 5,464,395 A | 11/1995 | Faxon et al. |
| 5,491,224 A | 2/1996 | Bittner et al. |
| 5,496,311 A | 3/1996 | Abele et al. |
| 5,499,630 A | 3/1996 | Hiki et al. |
| 5,507,724 A | 4/1996 | Hofmann et al. |
| 5,507,725 A | 4/1996 | Savage et al. |
| 5,538,504 A | 7/1996 | Linden et al. |
| 5,551,954 A | 9/1996 | Buscemi et al. |
| 5,554,182 A | 9/1996 | Dinh et al. |
| 5,570,693 A | 11/1996 | Jang et al. |
| 5,571,086 A | 11/1996 | Kaplan et al. |
| 5,571,151 A | 11/1996 | Gregory |
| 5,588,960 A | 12/1996 | Edwards et al. |
| 5,597,378 A | 1/1997 | Jervis |
| 5,599,300 A | 2/1997 | Weaver et al. |
| 5,614,204 A | 3/1997 | Cochrum |
| 5,628,784 A | 5/1997 | Strecker |
| 5,661,133 A | 8/1997 | Leiden et al. |
| 5,662,609 A | 9/1997 | Slepian |
| 5,662,711 A | 9/1997 | Douglas |
| 5,665,077 A | 9/1997 | Rosen et al. |
| 5,669,880 A | 9/1997 | Solar |
| 5,682,906 A | 11/1997 | Sterman et al. |
| 5,690,670 A | 11/1997 | Davidson |
| 5,693,029 A | 12/1997 | Leonhardt |
| 5,704,361 A | 1/1998 | Seward et al. |
| 5,704,926 A | 1/1998 | Sutton |
| 5,713,363 A | 2/1998 | Seward et al. |
| 5,713,853 A | 2/1998 | Clark et al. |
| 5,718,725 A | 2/1998 | Sterman et al. |
| 5,724,975 A | 3/1998 | Negus et al. |
| 5,724,977 A | 3/1998 | Yock et al. |
| 5,728,123 A | 3/1998 | Lemelson et al. |
| 5,735,847 A | 4/1998 | Gough et al. |
| 5,738,658 A | 4/1998 | Maus et al. |
| 5,743,874 A | 4/1998 | Fischell et al. |
| 5,755,682 A | 5/1998 | Knudson et al. |
| 5,756,696 A | 5/1998 | Gray et al. |
| 5,771,895 A | 6/1998 | Slager |
| 5,772,629 A | 6/1998 | Kaplan |
| 5,772,632 A | 6/1998 | Forman |
| 5,807,258 A | 9/1998 | Cimochowski et al. |
| 5,807,306 A | 9/1998 | Shapland et al. |
| 5,810,780 A | 9/1998 | Brimhall et al. |
| 5,814,005 A | 9/1998 | Barra et al. |
| 5,827,216 A | 10/1998 | Igo et al. |
| 5,830,222 A | 11/1998 | Makower |
| 5,830,224 A | 11/1998 | Cohn et al. |
| 5,836,913 A | 11/1998 | Orth et al. |
| 5,843,090 A | 12/1998 | Schuetz |
| 5,843,170 A | 12/1998 | Ahn |
| 5,944,738 A | 8/1999 | Amplatz et al. |
| 5,951,569 A | 9/1999 | Tuckey et al. |
| 5,989,280 A | 11/1999 | Euteneuer et al. |
| 6,019,788 A | 2/2000 | Butters et al. |
| 6,042,589 A | 3/2000 | Marianne |
| 6,053,891 A | 4/2000 | DeCampli |
| 6,081,738 A | 6/2000 | Hinohara et al. |
| 6,086,553 A | 7/2000 | Akbik |
| 6,092,526 A | 7/2000 | LaFontaine et al. |
| 6,095,878 A | 8/2000 | Van Balen |
| 6,113,612 A | 9/2000 | Swanson et al. |
| 6,120,494 A | 9/2000 | Jonkman |
| 6,120,522 A | 9/2000 | Vrba et al. |
| 6,120,534 A | 9/2000 | Ruiz |
| 6,152,937 A | 11/2000 | Peterson et al. |
| 6,165,185 A | 12/2000 | Shennib et al. |
| 6,168,620 B1 | 1/2001 | Kerr |
| 6,168,820 B1 | 1/2001 | Garwood et al. |
| 6,174,681 B1 | 1/2001 | Halling et al. |
| 6,190,353 B1 | 2/2001 | Makower et al. |
| 6,193,734 B1 | 2/2001 | Bolduc et al. |
| 6,196,230 B1 | 3/2001 | Hall et al. |
| 6,241,743 B1 | 6/2001 | Levin et al. |
| 6,248,117 B1 | 6/2001 | Blatter |
| 6,251,116 B1 | 6/2001 | Shennib et al. |
| 6,254,631 B1 | 7/2001 | Thompson |
| 6,280,412 B1 | 8/2001 | Pederson, Jr. et al. |

(56)                    References Cited

U.S. PATENT DOCUMENTS

| | | | |
|---|---|---|---|
| 6,283,951 | B1 | 9/2001 | Flaherty et al. |
| 6,287,332 | B1 | 9/2001 | Bolz et al. |
| 6,290,728 | B1 | 9/2001 | Phelps et al. |
| 6,302,875 | B1 | 10/2001 | Makower et al. |
| 6,302,892 | B1 | 10/2001 | Wilk |
| 6,302,905 | B1 | 10/2001 | Goldsteen et al. |
| 6,309,415 | B1 | 10/2001 | Pulnev et al. |
| 6,315,752 | B1 | 11/2001 | DiMatteo |
| 6,325,798 | B1 | 12/2001 | Edwards et al. |
| 6,361,545 | B1 | 3/2002 | Macoviak et al. |
| 6,375,615 | B1 | 4/2002 | Flaherty et al. |
| 6,387,116 | B1 | 5/2002 | Mckenzie et al. |
| 6,387,119 | B2 | 5/2002 | Wolf et al. |
| 6,391,036 | B1 | 5/2002 | Berg et al. |
| 6,402,767 | B1 | 6/2002 | Nash et al. |
| 6,443,158 | B1 | 9/2002 | LaFontaine et al. |
| 6,451,048 | B1 | 9/2002 | Berg et al. |
| 6,458,140 | B2 | 10/2002 | Akin et al. |
| 6,464,665 | B1 | 10/2002 | Heuser |
| 6,468,303 | B1 | 10/2002 | Amplatz et al. |
| 6,475,226 | B1 | 11/2002 | Belef et al. |
| 6,494,889 | B1 | 12/2002 | Fleischman et al. |
| 6,503,247 | B2 | 1/2003 | Swartz et al. |
| 6,506,201 | B2 | 1/2003 | Di Caprio et al. |
| 6,508,824 | B1 | 1/2003 | Flaherty et al. |
| 6,561,998 | B1 | 5/2003 | Roth et al. |
| 6,562,066 | B1 | 5/2003 | Martin |
| 6,565,542 | B2 | 5/2003 | Kumar et al. |
| 6,575,168 | B2 | 6/2003 | LaFontaine et al. |
| 6,579,311 | B1 | 6/2003 | Makower |
| 6,589,251 | B2 | 7/2003 | Yee et al. |
| 6,595,941 | B1 | 7/2003 | Blatter |
| 6,602,241 | B2 | 8/2003 | Makower et al. |
| 6,613,074 | B1 | 9/2003 | Mitelberg et al. |
| 6,616,624 | B1 | 9/2003 | Kieval |
| 6,616,675 | B1 | 9/2003 | Evard et al. |
| 6,620,202 | B2 | 9/2003 | Bottcher et al. |
| 6,623,494 | B1 | 9/2003 | Blatter |
| 6,626,920 | B2 | 9/2003 | Whayne |
| 6,638,293 | B1 | 10/2003 | Makower et al. |
| 6,692,482 | B2 | 2/2004 | Heller et al. |
| 6,695,878 | B2 | 2/2004 | McGuckin, Jr. et al. |
| 6,699,256 | B1 | 3/2004 | Logan et al. |
| 6,702,828 | B2 | 3/2004 | Whayne |
| 6,709,414 | B2 | 3/2004 | Weitzel et al. |
| 6,709,444 | B1 | 3/2004 | Makower |
| 6,712,836 | B1 | 3/2004 | Berg et al. |
| 6,719,804 | B2 | 4/2004 | St. Pierre |
| 6,726,659 | B1 | 4/2004 | Stocking et al. |
| 6,726,677 | B1 | 4/2004 | Flaherty et al. |
| 6,736,825 | B2 | 5/2004 | Blatter et al. |
| 6,740,426 | B2 | 5/2004 | Kawachi et al. |
| 6,743,244 | B2 | 6/2004 | Blatter et al. |
| 6,743,259 | B2 | 6/2004 | Ginn |
| 6,746,426 | B1 | 6/2004 | Flaherty et al. |
| 6,748,484 | B1 | 6/2004 | Henderson et al. |
| 6,758,854 | B1 | 7/2004 | Butler et al. |
| 6,776,785 | B1 | 8/2004 | Yencho et al. |
| 6,797,083 | B2 | 9/2004 | Peterson |
| 6,802,858 | B2 | 10/2004 | Gambale et al. |
| 6,805,706 | B2 | 10/2004 | Solovay et al. |
| 6,808,498 | B2 | 10/2004 | Laroya et al. |
| 6,827,698 | B1 | 12/2004 | Kleinekofort |
| 6,847,348 | B2 | 1/2005 | Rojewski |
| 6,854,172 | B2 | 2/2005 | Kaese et al. |
| 6,858,035 | B2 | 2/2005 | Whayne |
| 6,869,437 | B1 | 3/2005 | Hausen et al. |
| 6,893,413 | B2 | 5/2005 | Martin |
| 6,913,600 | B2 | 7/2005 | Valley et al. |
| 6,913,607 | B2 | 7/2005 | Ainsworth et al. |
| 6,915,154 | B1 | 7/2005 | Docherty et al. |
| 6,926,690 | B2 | 8/2005 | Renati |
| 6,928,313 | B2 | 8/2005 | Peterson |
| 6,972,023 | B2 | 12/2005 | Whayne et al. |
| 6,979,351 | B2 | 12/2005 | Forsell et al. |
| 6,985,774 | B2 | 1/2006 | Kieval et al. |
| 7,002,491 | B2 | 2/2006 | Robbins |
| 7,008,397 | B2 | 3/2006 | Tweden et al. |
| 7,011,094 | B2 | 3/2006 | Rapacki et al. |
| 7,011,678 | B2 | 3/2006 | Tenerz et al. |
| 7,025,741 | B2 | 4/2006 | Cull |
| 7,025,746 | B2 | 4/2006 | Tal |
| 7,037,329 | B2 | 5/2006 | Martin |
| 7,056,294 | B2 | 6/2006 | Khairkhahan et al. |
| 7,056,320 | B2 | 6/2006 | Utley et al. |
| 7,056,325 | B1 | 6/2006 | Makower et al. |
| 7,077,860 | B2 | 7/2006 | Yan et al. |
| 7,083,631 | B2 | 8/2006 | Houser et al. |
| 7,108,701 | B2 | 9/2006 | Evens et al. |
| 7,115,136 | B2 | 10/2006 | Park et al. |
| 7,118,546 | B2 | 10/2006 | Blatter |
| 7,128,750 | B1 | 10/2006 | Stergiopulos |
| 7,175,644 | B2 | 2/2007 | Cooper et al. |
| 7,182,771 | B1 | 2/2007 | Houser et al. |
| 7,235,095 | B2 | 6/2007 | Haverkost et al. |
| 7,294,115 | B1 | 11/2007 | Wilk |
| 7,316,706 | B2 | 1/2008 | Bloom et al. |
| 7,317,951 | B2 | 1/2008 | Schneider et al. |
| 7,318,804 | B2 | 1/2008 | Weitzel et al. |
| 7,326,221 | B2 | 2/2008 | Sakamoto et al. |
| 7,331,985 | B2 | 2/2008 | Thompson et al. |
| 7,335,220 | B2 | 2/2008 | Khosravi et al. |
| 7,351,247 | B2 | 4/2008 | Kupiecki et al. |
| 7,361,181 | B2 | 4/2008 | Hindrichs et al. |
| 7,374,567 | B2 | 5/2008 | Heuser |
| D581,054 | S | 11/2008 | Moore |
| 7,462,162 | B2 | 12/2008 | Phan et al. |
| 7,476,200 | B2 | 1/2009 | Tal |
| 7,530,963 | B2 | 5/2009 | Albright |
| 7,563,277 | B2 | 7/2009 | Case et al. |
| 7,623,926 | B2 | 11/2009 | Rossing et al. |
| 7,625,593 | B2 | 12/2009 | Mandrusov et al. |
| 7,628,768 | B2 | 12/2009 | Faul et al. |
| D612,499 | S | 3/2010 | Ondracek et al. |
| 7,691,110 | B2 | 4/2010 | Secrest et al. |
| 7,699,863 | B2 | 4/2010 | Marco et al. |
| 7,722,549 | B2 | 5/2010 | Nakao |
| 7,722,665 | B2 | 5/2010 | Anwar et al. |
| 7,744,621 | B2 | 6/2010 | Paul et al. |
| 7,794,495 | B2 | 9/2010 | Gale et al. |
| 7,807,191 | B2 | 10/2010 | Iyer et al. |
| 7,815,590 | B2 | 10/2010 | Cooper |
| 7,815,656 | B2 | 10/2010 | Rust et al. |
| 7,815,852 | B2 | 10/2010 | Sternby |
| 7,828,814 | B2 | 11/2010 | Brenneman et al. |
| 7,846,179 | B2 | 12/2010 | Belef et al. |
| 7,846,194 | B2 | 12/2010 | Hartley et al. |
| 7,850,705 | B2 | 12/2010 | Bachinski et al. |
| 7,867,547 | B2 | 1/2011 | Tochterman et al. |
| 7,879,367 | B2 | 2/2011 | Heublein et al. |
| 7,892,246 | B2 | 2/2011 | Akin et al. |
| 7,892,247 | B2 | 2/2011 | Conston et al. |
| 7,923,022 | B2 | 4/2011 | Wang et al. |
| 7,951,194 | B2 | 5/2011 | Gueriguian et al. |
| 7,959,603 | B2 | 6/2011 | Wahr et al. |
| 7,964,210 | B2 | 6/2011 | Wang et al. |
| 7,967,769 | B2 | 6/2011 | Faul et al. |
| 7,972,346 | B2 | 7/2011 | Bachmann et al. |
| 8,002,821 | B2 | 8/2011 | Stinson |
| 8,016,782 | B2 | 9/2011 | Brenneman et al. |
| 8,029,470 | B2 | 10/2011 | Whiting et al. |
| 8,048,150 | B2 | 11/2011 | Weber et al. |
| 8,052,751 | B2 | 11/2011 | Aklog et al. |
| 8,057,534 | B2 | 11/2011 | Boismier et al. |
| 8,070,708 | B2 | 12/2011 | Rottenberg et al. |
| 8,088,171 | B2 | 1/2012 | Brenneman |
| 8,089,029 | B2 | 1/2012 | Flanagan |
| 8,091,556 | B2 | 1/2012 | Keren et al. |
| 8,128,689 | B2 | 3/2012 | Weber et al. |
| 8,152,773 | B2 | 4/2012 | Albrecht et al. |
| 8,182,527 | B2 | 5/2012 | Llanos et al. |
| 8,214,015 | B2 | 7/2012 | Macaulay et al. |
| 8,221,495 | B2 | 7/2012 | Shrivastava et al. |
| 8,226,592 | B2 | 7/2012 | Brenneman et al. |

(56) References Cited

U.S. PATENT DOCUMENTS

| | | | |
|---|---|---|---|
| D665,500 S | 8/2012 | Martin et al. |
| 8,282,591 B2 | 10/2012 | Khan et al. |
| 8,308,682 B2 | 11/2012 | Kramer et al. |
| 8,357,193 B2 | 1/2013 | Phan et al. |
| 8,376,979 B2 | 2/2013 | Kapadia |
| 8,382,697 B2 | 2/2013 | Brenneman et al. |
| D679,015 S | 3/2013 | Nakaji |
| 8,409,167 B2 | 4/2013 | Roschak |
| 8,500,697 B2 | 8/2013 | Kurth et al. |
| 8,506,984 B2 | 8/2013 | Cook et al. |
| 8,518,062 B2 | 8/2013 | Cole et al. |
| 8,518,662 B2 | 8/2013 | Ritzen et al. |
| 8,545,552 B2 | 10/2013 | Garrison et al. |
| 8,641,724 B2 | 2/2014 | Brenneman et al. |
| 8,657,790 B2 | 2/2014 | Tal et al. |
| 8,696,611 B2 | 4/2014 | Nitzan et al. |
| D705,427 S | 5/2014 | Jagger et al. |
| 8,768,487 B2 | 7/2014 | Farnan et al. |
| 8,784,860 B2 | 7/2014 | Falotico et al. |
| 8,852,207 B2 | 10/2014 | Simpson et al. |
| 8,882,830 B2 | 11/2014 | Cartledge et al. |
| 8,920,449 B2 | 12/2014 | Wilkinson |
| 8,926,545 B2 | 1/2015 | Brenneman et al. |
| 8,932,341 B2 | 1/2015 | Brenneman |
| D723,166 S | 2/2015 | Igaki et al. |
| 8,951,276 B2 | 2/2015 | Kellerman et al. |
| 9,005,155 B2 | 4/2015 | Sugimoto |
| 9,044,588 B2 | 6/2015 | Conn |
| 9,061,115 B2 | 6/2015 | Ward et al. |
| 9,067,050 B2 | 6/2015 | Gallagher et al. |
| 9,198,756 B2 | 12/2015 | Aklog et al. |
| 9,232,997 B2 | 1/2016 | Sugimoto et al. |
| 9,277,995 B2 | 3/2016 | Celermajer et al. |
| 9,345,485 B2 | 5/2016 | Dakin et al. |
| 9,439,746 B2 | 9/2016 | Bell et al. |
| 9,456,812 B2 | 10/2016 | Finch et al. |
| 9,550,022 B2 | 1/2017 | Brenneman et al. |
| 9,649,480 B2 | 5/2017 | Sugimoto et al. |
| 9,655,666 B2 | 5/2017 | Markowitz et al. |
| 9,681,948 B2 | 6/2017 | Levi et al. |
| 9,693,800 B2 | 7/2017 | Aman et al. |
| 9,775,636 B2 | 10/2017 | Fazio et al. |
| 9,789,294 B2 | 10/2017 | Taft et al. |
| 9,814,483 B2 | 11/2017 | Vardi |
| 9,827,404 B2 | 11/2017 | Nance et al. |
| 9,839,517 B2 | 12/2017 | Centola et al. |
| 9,872,981 B2 | 1/2018 | Sparks et al. |
| 9,980,815 B2 | 5/2018 | Nitzan et al. |
| 10,076,403 B1 | 9/2018 | Eigler et al. |
| 10,130,371 B2 | 11/2018 | Dehdashtian et al. |
| 10,272,230 B2 | 4/2019 | Malek et al. |
| 10,292,690 B2 | 5/2019 | Celermajer et al. |
| 10,327,746 B2 | 6/2019 | Glimsdale et al. |
| 10,413,284 B2 | 9/2019 | McNamara et al. |
| 10,426,482 B2 | 10/2019 | Rafiee et al. |
| 10,426,497 B2 | 10/2019 | Chou et al. |
| 10,433,851 B2 | 10/2019 | Adams et al. |
| 10,456,259 B2 | 10/2019 | Subramanian et al. |
| 10,543,113 B2 | 1/2020 | Vong et al. |
| 10,561,423 B2 | 2/2020 | Sharma |
| 10,565,835 B2 | 2/2020 | Harrington et al. |
| 10,568,751 B2 | 2/2020 | McNamara |
| 10,595,999 B2 | 3/2020 | Vettukattil et al. |
| 10,709,451 B2 | 7/2020 | Gronberg et al. |
| 10,835,394 B2 | 11/2020 | Nae et al. |
| 10,898,698 B1 | 1/2021 | Eigler et al. |
| 10,925,731 B2 | 2/2021 | Bishop et al. |
| 10,925,756 B2 | 2/2021 | Perszyk |
| 10,940,296 B2 | 3/2021 | Keren |
| 11,135,054 B2 | 10/2021 | Nitzan et al. |
| 11,135,410 B2 | 10/2021 | Finch et al. |
| 11,234,702 B1 | 2/2022 | Eigler et al. |
| 11,291,807 B2 | 4/2022 | Eigler et al. |
| 11,298,117 B2 | 4/2022 | Hariton et al. |
| 11,304,698 B2 | 4/2022 | Sharma |

| | | | | |
|---|---|---|---|---|
| 11,395,644 B2 | 7/2022 | Alanbaei | | |
| 11,420,034 B2 | 8/2022 | Solomon et al. | | |
| 2001/0000041 A1 | 3/2001 | Selmon et al. | | |
| 2001/0025643 A1 | 10/2001 | Foley | | |
| 2001/0045698 A1 | 11/2001 | Lo | | |
| 2002/0013616 A1 | 1/2002 | Carter et al. | | |
| 2002/0029079 A1 | 3/2002 | Kim et al. | | |
| 2002/0062146 A1 | 5/2002 | Makower et al. | | |
| 2002/0169466 A1 | 11/2002 | Peterson et al. | | |
| 2002/0193751 A1 | 12/2002 | Theeuwes et al. | | |
| 2003/0017150 A1 | 1/2003 | Torphy | | |
| 2003/0060876 A1 | 3/2003 | Loshakove et al. | | |
| 2003/0065345 A1 | 4/2003 | Weadock | | |
| 2003/0181928 A1 | 9/2003 | Vidlund et al. | | |
| 2003/0225425 A1 | 12/2003 | Kupiecki et al. | | |
| 2004/0064081 A1 | 4/2004 | Stanish | | |
| 2004/0087997 A1 | 5/2004 | Brenneman | | |
| 2004/0092879 A1 | 5/2004 | Kraus et al. | | |
| 2004/0098105 A1 | 5/2004 | Stinson et al. | | |
| 2004/0215168 A1 | 10/2004 | Verrier et al. | | |
| 2004/0215220 A1 | 10/2004 | Dolan et al. | | |
| 2004/0215228 A1* | 10/2004 | Simpson | A61M 25/10 | |
| | | | 606/194 | |
| 2004/0215323 A1 | 10/2004 | Stiger | | |
| 2004/0230156 A1 | 11/2004 | Schreck et al. | | |
| 2004/0260318 A1 | 12/2004 | Hunter et al. | | |
| 2005/0021085 A1 | 1/2005 | Abrams et al. | | |
| 2005/0038501 A1 | 2/2005 | Moore et al. | | |
| 2005/0043708 A1 | 2/2005 | Gleeson et al. | | |
| 2005/0049675 A1 | 3/2005 | Wallace | | |
| 2005/0060041 A1 | 3/2005 | Phan et al. | | |
| 2005/0075655 A1 | 4/2005 | Bumbalough et al. | | |
| 2005/0075656 A1 | 4/2005 | Beaupre | | |
| 2005/0082226 A1 | 4/2005 | Bene et al. | | |
| 2005/0107723 A1 | 5/2005 | Wehman et al. | | |
| 2005/0149096 A1 | 7/2005 | Hilal et al. | | |
| 2005/0165344 A1 | 7/2005 | Dobak | | |
| 2005/0228402 A1 | 10/2005 | Hofmann | | |
| 2005/0249770 A1 | 11/2005 | Hunter | | |
| 2005/0249776 A1 | 11/2005 | Chen et al. | | |
| 2005/0272806 A1 | 12/2005 | Falotico et al. | | |
| 2006/0024359 A1 | 2/2006 | Walker et al. | | |
| 2006/0034466 A1 | 2/2006 | Form et al. | | |
| 2006/0111704 A1 | 5/2006 | Brenneman et al. | | |
| 2006/0130591 A1 | 6/2006 | Perkins | | |
| 2006/0130767 A1 | 6/2006 | Herchen | | |
| 2006/0182536 A1 | 8/2006 | Rice et al. | | |
| 2006/0198869 A1 | 9/2006 | Furst et al. | | |
| 2006/0241342 A1 | 10/2006 | Macaulay et al. | | |
| 2006/0258980 A1* | 11/2006 | Bridges | A61M 25/1011 | |
| | | | 604/101.05 | |
| 2006/0264801 A1 | 11/2006 | Bolling et al. | | |
| 2006/0271196 A1 | 11/2006 | Saal et al. | | |
| 2006/0293701 A1 | 12/2006 | Ainsworth et al. | | |
| 2007/0083258 A1 | 4/2007 | Falotico et al. | | |
| 2007/0173787 A1 | 7/2007 | Huang et al. | | |
| 2007/0179426 A1 | 8/2007 | Selden | | |
| 2007/0213750 A1 | 9/2007 | Weadock | | |
| 2008/0021485 A1 | 1/2008 | Catanese et al. | | |
| 2008/0051883 A1 | 2/2008 | Llanos et al. | | |
| 2008/0065009 A1 | 3/2008 | Ben-Muvhar | | |
| 2008/0091264 A1 | 4/2008 | Machold et al. | | |
| 2008/0109069 A1 | 5/2008 | Coleman et al. | | |
| 2008/0161904 A1 | 7/2008 | Heuser et al. | | |
| 2008/0167595 A1 | 7/2008 | Porter et al. | | |
| 2008/0234842 A1 | 9/2008 | Zhang | | |
| 2009/0125097 A1 | 5/2009 | Bruszewski et al. | | |
| 2009/0143713 A1 | 6/2009 | Van Dam et al. | | |
| 2009/0149947 A1 | 6/2009 | Frohwitter | | |
| 2009/0187116 A1 | 7/2009 | Noishiki et al. | | |
| 2009/0281379 A1 | 11/2009 | Binmoeller et al. | | |
| 2010/0030321 A1 | 2/2010 | Mach | | |
| 2010/0106171 A1 | 4/2010 | Arepally et al. | | |
| 2010/0198041 A1 | 8/2010 | Christian et al. | | |
| 2010/0217382 A1 | 8/2010 | Chau et al. | | |
| 2010/0298930 A1 | 11/2010 | Orlov | | |
| 2011/0096036 A1 | 4/2011 | McIntosh et al. | | |
| 2011/0106118 A1 | 5/2011 | Son et al. | | |
| 2011/0251482 A1 | 10/2011 | Kellerman et al. | | |

(56)　　　　References Cited

U.S. PATENT DOCUMENTS

| | | |
|---|---|---|
| 2012/0041544 A1 | 2/2012 | Wolf |
| 2012/0053686 A1 | 3/2012 | McNamara et al. |
| 2012/0143141 A1 | 6/2012 | Verkaik et al. |
| 2012/0265229 A1 | 10/2012 | Rottenberg et al. |
| 2013/0022214 A1 | 1/2013 | Dickins et al. |
| 2013/0030521 A1 | 1/2013 | Nitzan et al. |
| 2013/0178784 A1 | 7/2013 | McNamara et al. |
| 2013/0253342 A1 | 9/2013 | Griswold et al. |
| 2013/0261531 A1* | 10/2013 | Gallagher ......... A61M 5/16813 |
| | | 604/9 |
| 2013/0281988 A1 | 10/2013 | Magnin et al. |
| 2014/0183828 A1 | 7/2014 | Xu et al. |
| 2014/0203939 A1 | 7/2014 | Harrington et al. |
| 2014/0222040 A1 | 8/2014 | Park et al. |
| 2014/0276395 A1 | 9/2014 | Wilson et al. |
| 2014/0277054 A1 | 9/2014 | McNamara et al. |
| 2014/0278442 A1 | 9/2014 | Hong et al. |
| 2015/0119796 A1 | 4/2015 | Finch |
| 2015/0148731 A1 | 5/2015 | Mcnamara et al. |
| 2015/0151101 A1 | 6/2015 | Bonnette et al. |
| 2015/0238729 A1 | 8/2015 | Jenson et al. |
| 2016/0022293 A1 | 1/2016 | Dubrul et al. |
| 2016/0022970 A1 | 1/2016 | Forcucci et al. |
| 2016/0058452 A1 | 3/2016 | Brenneman et al. |
| 2016/0120550 A1 | 5/2016 | McNamara et al. |
| 2016/0220357 A1 | 8/2016 | Anand et al. |
| 2016/0270810 A1 | 9/2016 | Vardi et al. |
| 2016/0296317 A1 | 10/2016 | Timmermans et al. |
| 2016/0323977 A1 | 11/2016 | Sun et al. |
| 2017/0090865 A1 | 3/2017 | Armstrong-Muntner et al. |
| 2017/0106176 A1* | 4/2017 | Taft .................... A61M 27/008 |
| 2017/0113026 A1 | 4/2017 | Finch |
| 2017/0128705 A1 | 5/2017 | Forcucci et al. |
| 2017/0303959 A1 | 10/2017 | Feng et al. |
| 2017/0319823 A1 | 11/2017 | Yacoby et al. |
| 2017/0340460 A1 | 11/2017 | Rosen et al. |
| 2018/0177516 A1 | 6/2018 | Vardi et al. |
| 2018/0256904 A1 | 9/2018 | Li et al. |
| 2019/0008628 A1 | 1/2019 | Eigler et al. |
| 2019/0269392 A1 | 9/2019 | Celermajer et al. |
| 2019/0298909 A1 | 10/2019 | Cully et al. |
| 2020/0054867 A1 | 2/2020 | Schwartz et al. |
| 2020/0085600 A1 | 3/2020 | Schwartz et al. |
| 2020/0101270 A1 | 4/2020 | Sutherland |
| 2020/0170662 A1 | 6/2020 | Vardi et al. |
| 2020/0187945 A1 | 6/2020 | Rowe et al. |
| 2020/0254228 A1 | 8/2020 | Taft et al. |
| 2020/0261704 A1 | 8/2020 | Wang et al. |
| 2020/0289196 A1 | 9/2020 | Arevalos et al. |
| 2020/0315599 A1 | 10/2020 | Nae et al. |
| 2020/0368505 A1 | 11/2020 | Nae et al. |
| 2020/0391016 A1 | 12/2020 | Passman et al. |
| 2021/0007790 A1 | 1/2021 | Takahashi et al. |
| 2021/0007791 A1 | 1/2021 | Takahashi et al. |
| 2021/0007800 A1 | 1/2021 | Takahashi et al. |
| 2021/0045691 A1 | 2/2021 | Zou et al. |
| 2021/0059650 A1 | 3/2021 | Eidenschink et al. |
| 2021/0077186 A1 | 3/2021 | Pate et al. |
| 2021/0085935 A1 | 3/2021 | Fahey et al. |
| 2021/0092522 A1 | 3/2021 | Draper et al. |
| 2021/0121179 A1 | 4/2021 | Ben-David et al. |
| 2021/0153776 A1 | 5/2021 | Minar et al. |
| 2021/0161637 A1 | 6/2021 | Eigler et al. |
| 2021/0177508 A1 | 6/2021 | Kellerman |
| 2021/0236138 A1 | 8/2021 | Perszyk et al. |
| 2021/0290214 A1 | 9/2021 | Cole et al. |
| 2021/0369321 A1 | 12/2021 | Yang et al. |
| 2021/0401494 A1 | 12/2021 | Passman et al. |
| 2022/0001154 A1 | 1/2022 | Rowe et al. |
| 2022/0008014 A1 | 1/2022 | Rowe et al. |
| 2022/0031327 A1 | 2/2022 | Manash et al. |
| 2022/0039667 A1 | 2/2022 | Schmitt et al. |
| 2022/0039671 A1 | 2/2022 | Fahey |
| 2022/0039833 A1 | 2/2022 | Thai et al. |
| 2022/0088355 A1 | 3/2022 | Rabito et al. |
| 2022/0096087 A1 | 3/2022 | Valdez |
| 2022/0110679 A1 | 4/2022 | Wang et al. |
| 2022/0142652 A1 | 5/2022 | Alexander et al. |
| 2022/0151784 A1 | 5/2022 | Eigler et al. |
| 2022/0168015 A1 | 6/2022 | Murray et al. |
| 2022/0184356 A1 | 6/2022 | Nae et al. |
| 2022/0202443 A1 | 6/2022 | Thai et al. |
| 2022/0203078 A1 | 6/2022 | May |
| 2022/0211380 A1 | 7/2022 | Pate |
| 2022/0218352 A1 | 7/2022 | O'Halloran et al. |
| 2022/0218964 A1 | 7/2022 | Fahey et al. |
| 2022/0241564 A1 | 8/2022 | Shang et al. |
| 2022/0241565 A1 | 8/2022 | Nae et al. |
| 2022/0257904 A1 | 8/2022 | Passman et al. |
| 2022/0273279 A1 | 9/2022 | Valdez et al. |
| 2022/0280160 A1 | 9/2022 | Sharma |
| 2022/0280760 A1 | 9/2022 | Thai et al. |
| 2022/0296865 A1 | 9/2022 | Rafiee et al. |
| 2022/0313234 A1 | 10/2022 | Mcnamara et al. |
| 2022/0323012 A1 | 10/2022 | Pool et al. |
| 2022/0323196 A1 | 10/2022 | Rafiee et al. |
| 2022/0346936 A1 | 11/2022 | Scutti et al. |
| 2022/0347446 A1 | 11/2022 | Fahey et al. |
| 2022/0370120 A1 | 11/2022 | Yang et al. |
| 2022/0379100 A1 | 12/2022 | Gutierrez et al. |
| 2022/0387009 A1 | 12/2022 | Bukhdruker et al. |
| 2023/0099410 A1 | 3/2023 | Primeaux |
| 2023/0165672 A1 | 6/2023 | Fahey et al. |
| 2023/0181214 A1 | 6/2023 | Vardi et al. |
| 2023/0191093 A1 | 6/2023 | Nae et al. |
| 2023/0263949 A1 | 8/2023 | Passman et al. |
| 2023/0285133 A1 | 9/2023 | Eigler et al. |
| 2023/0330398 A1 | 10/2023 | Nae et al. |

FOREIGN PATENT DOCUMENTS

| | | |
|---|---|---|
| WO | 2022031317 A1 | 2/2022 |
| WO | 2022060630 A1 | 3/2022 |
| WO | 2022133070 A1 | 6/2022 |
| WO | 2022169865 A1 | 8/2022 |
| WO | 2022177737 A1 | 8/2022 |
| WO | 2022197454 A1 | 9/2022 |
| WO | 2022197455 A1 | 9/2022 |
| WO | 2022232133 A1 | 11/2022 |
| WO | 2022246158 A1 | 11/2022 |
| WO | 2022246166 A1 | 11/2022 |
| WO | 2022271473 A1 | 12/2022 |
| WO | 2023022883 A1 | 2/2023 |
| WO | 2023027926 A1 | 3/2023 |
| WO | 2023079498 A1 | 5/2023 |
| WO | 2023081127 A1 | 5/2023 |
| WO | 2023081129 A1 | 5/2023 |
| WO | 2023154235 A1 | 8/2023 |
| WO | 2023154308 A1 | 8/2023 |
| WO | 2023172435 A1 | 9/2023 |
| WO | 2023172436 A1 | 9/2023 |
| WO | 2023196243 A1 | 10/2023 |
| WO | 2023239784 A1 | 12/2023 |
| WO | 2023239785 A1 | 12/2023 |
| WO | 2023239788 A2 | 12/2023 |

OTHER PUBLICATIONS

Mahmood et al. "Applications of the Distal Anchoring Technique in Coronary and Peripheral Interventions", Cath Lab Digest, vol. 19, Issue 10, Oct. 4, 2011 [Online], [Retrieved on Jan. 23, 2019]. Retrieved from the Internet: <https://www.cathlabdigest.com/articles/Applications-Distal-Anchoring-Technique-Coronary-Peripheral-Interventions>.

Emil Mantini, MD, et al., Title: Congenital Anomalies Involving the Coronary Sinus, Circulation, Journal of the American Heart Association, vol. XXXIII, Feb. 1966, pp. 317-327.

Kong, et al.—Creation Of An Intra-atrial Communication With A New Amplatzer Shunt Prosthesis, Catheterization and Cardiovascular Interventions 56:267-271 (2002).

(56) References Cited

OTHER PUBLICATIONS

P.K. Kong, et al., Title: Unroofed Coronary Sinus and Persistent Left Superior Vena Cava, The European Society of Cardiology, 2006, pp. 398401.
Ruebben et al., "Arteriovenous fistulas induced by femoral arterial catheterization: percuntaneous treatment," Radiology, 209:729, 1998.
Vandhana Scheller, et al., Title: Coronary Sinus to Left Atrial Communication, Case Report in Medicine, Ohio Heart and Vascular Center, vol. 2009, Article ID 790715, pp. 13.

* cited by examiner

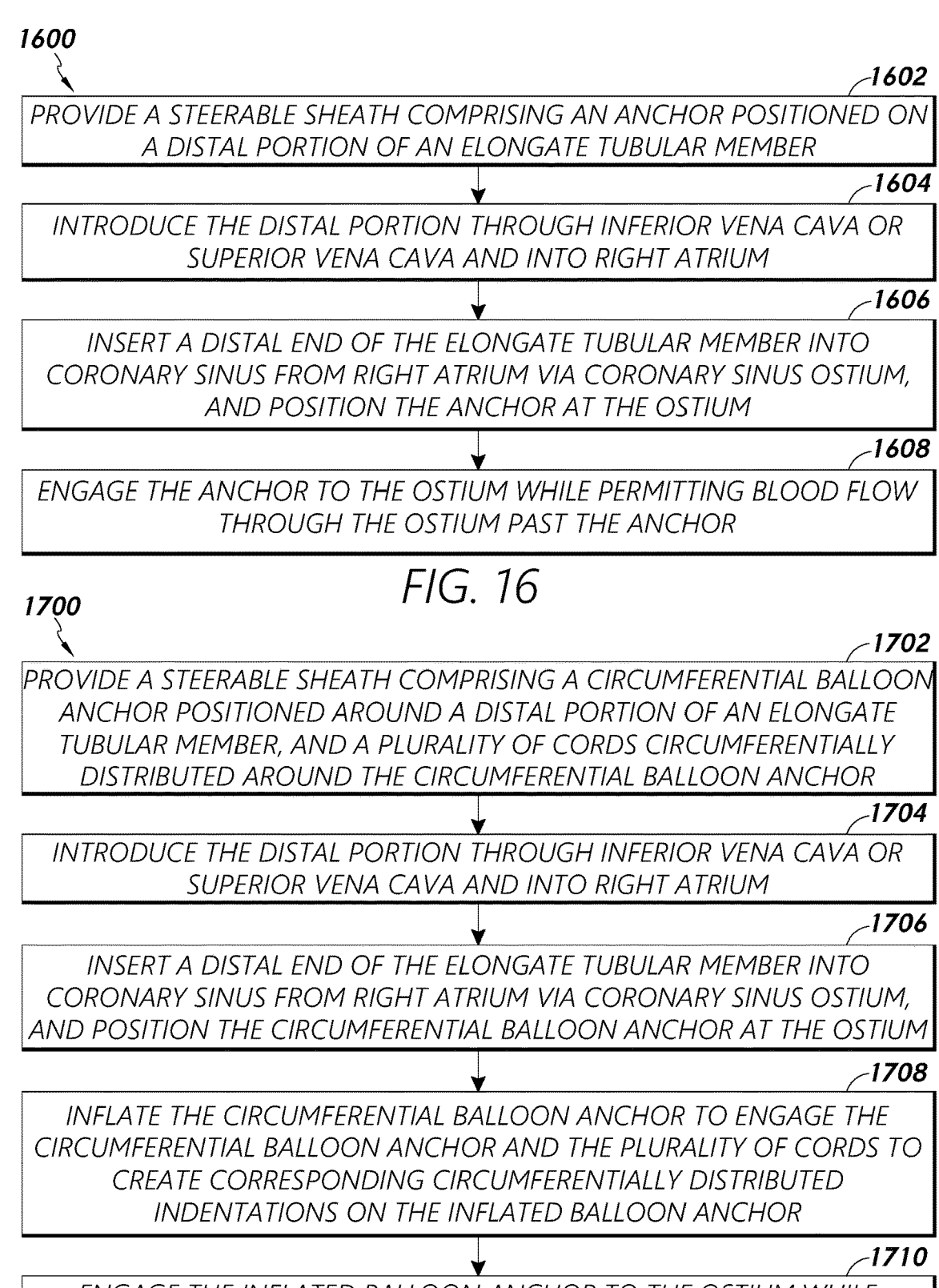

*1600*

*1602*
PROVIDE A STEERABLE SHEATH COMPRISING AN ANCHOR POSITIONED ON A DISTAL PORTION OF AN ELONGATE TUBULAR MEMBER

*1604*
INTRODUCE THE DISTAL PORTION THROUGH INFERIOR VENA CAVA OR SUPERIOR VENA CAVA AND INTO RIGHT ATRIUM

*1606*
INSERT A DISTAL END OF THE ELONGATE TUBULAR MEMBER INTO CORONARY SINUS FROM RIGHT ATRIUM VIA CORONARY SINUS OSTIUM, AND POSITION THE ANCHOR AT THE OSTIUM

*1608*
ENGAGE THE ANCHOR TO THE OSTIUM WHILE PERMITTING BLOOD FLOW THROUGH THE OSTIUM PAST THE ANCHOR

*1702*
PROVIDE A STEERABLE SHEATH COMPRISING A CIRCUMFERENTIAL BALLOON ANCHOR POSITIONED AROUND A DISTAL PORTION OF AN ELONGATE TUBULAR MEMBER, AND A PLURALITY OF CORDS CIRCUMFERENTIALLY DISTRIBUTED AROUND THE CIRCUMFERENTIAL BALLOON ANCHOR

*1704*
INTRODUCE THE DISTAL PORTION THROUGH INFERIOR VENA CAVA OR SUPERIOR VENA CAVA AND INTO RIGHT ATRIUM

*1706*
INSERT A DISTAL END OF THE ELONGATE TUBULAR MEMBER INTO CORONARY SINUS FROM RIGHT ATRIUM VIA CORONARY SINUS OSTIUM, AND POSITION THE CIRCUMFERENTIAL BALLOON ANCHOR AT THE OSTIUM

*1708*
INFLATE THE CIRCUMFERENTIAL BALLOON ANCHOR TO ENGAGE THE CIRCUMFERENTIAL BALLOON ANCHOR AND THE PLURALITY OF CORDS TO CREATE CORRESPONDING CIRCUMFERENTIALLY DISTRIBUTED INDENTATIONS ON THE INFLATED BALLOON ANCHOR

*1710*
ENGAGE THE INFLATED BALLOON ANCHOR TO THE OSTIUM WHILE PERMITTING BLOOD FLOW THROUGH THE OSTIUM ALONG THE INDENTATIONS

*FIG. 17*

ANCHOR FOR TRANSCATHETER ACCESS INTO THE CORONARY SINUS

CROSS REFERENCE TO RELATED APPLICATIONS

This application is a continuation application of International Patent Application Serial No. PCT/US2020/027147, filed Apr. 8, 2020 and entitled ANCHOR FOR TRANS-CATHETER ACCESS INTO THE CORONARY SINUS, which claims priority based on U.S. Provisional Patent Application Ser. No. 62/836,851, filed Apr. 22, 2019 and entitled ANCHOR FOR TRANSCATHETER ACCESS INTO THE CORONARY SINUS, the full disclosures of both of which are hereby expressly incorporated by reference herein in their entireties for all purposes.

BACKGROUND

Field

The present disclosure generally relates to the field of delivering medical implant devices and/or therapies.

Description of Related Art

Transcatheter delivery of implant devices and/or therapies to the heart can be performed to address various heart abnormalities. Delivery of implant devices and/or therapies to the heart can be performed for treatment of elevate pressure in the left atrium.

SUMMARY

Described herein are methods and devices for providing stable transcatheter access into the coronary sinus from the right atrium via the coronary sinus ostium. In some implementations, the present disclosure relates to a steerable sheath comprising an elongate tubular member which includes an inner lumen configured to receive a plurality of instruments, and a partially circumferential balloon anchor disposed partially circumferentially on a distal portion of the elongate tubular member. The partially circumferential balloon anchor can include a proximal balloon portion and a distal balloon portion. When the partially circumferential balloon anchor is in an inflated state, the distal balloon portion can have a tapered longitudinal profile tapering toward a distal end of the partially circumferential balloon anchor, and the partially circumferential balloon anchor can be configured to, while positioned to engage with a coronary sinus, permit blood flow through an ostium of the coronary sinus.

In some embodiments, the partially circumferential balloon anchor, in the inflated state, is configured to be positioned to engage with both the ostium and a portion of the coronary sinus adjacent to the ostium.

In some embodiments, the tapered longitudinal profile comprises a convex curvature.

In some embodiments, the partially circumferential balloon anchor is positioned around less than 50% of a circumference of the distal portion of the elongate tubular member.

In some embodiments, the partially circumferential balloon anchor comprises a textured exterior surface configured to engage with the ostium and a portion of the coronary sinus adjacent to the ostium. The textured exterior surface can comprise either or both of a plurality of bumps and a plurality of ridges.

In some embodiments, the proximal balloon portion extends laterally from the distal portion of the elongate tubular member, a deformable panel being coupled to the proximal balloon portion.

In some embodiments, the inner lumen is configured to receive a therapy device delivery catheter carrying a therapy device for deployment to a heart location. The therapy device can comprise a shunt device for deployment onto a left atrial wall.

In some implementations, a steerable sheath comprises an elongate tubular member which includes an inner lumen configured to receive a plurality of instruments, and a circumferential balloon anchor disposed circumferentially around a distal portion of the elongate tubular member. A plurality of cords can be circumferentially distributed around the circumferential balloon anchor. When the circumferential balloon anchor is in an inflated state, the plurality of cords can be configured to engage the circumferential balloon anchor to create corresponding circumferentially distributed indentations on the circumferential balloon anchor, and the circumferential balloon anchor can be configured to, while positioned to engage with a coronary sinus, permit blood flow through an ostium of the coronary sinus along a path defined at least in part by the circumferentially distributed indentations.

In some embodiments, the circumferential balloon anchor, in the inflated state, is configured to be positioned to engage with the ostium.

In some embodiments, the circumferential balloon anchor comprises a proximal balloon portion and a distal balloon portion, and respective distal ends of the plurality of cords are coupled to corresponding locations on the distal balloon portion, the plurality of cords being movable relative to the elongate tubular member along a longitudinal axis of the elongate tubular member. Moving the plurality of cords proximally relative to the elongate tubular member can be configured to engage the circumferential balloon anchor in the inflated state with the plurality of cords to provide the corresponding circumferentially distributed indentations. In some embodiments, the plurality of cords comprises five cords.

In some embodiments, the distal balloon portion comprises a tapered longitudinal profile tapering toward a distal end of the circumferential balloon anchor, the distal balloon portion being configured to engage with the ostium and a portion of the coronary sinus adjacent to the ostium.

In some embodiments, the circumferential balloon anchor comprises a textured exterior surface configured to engage with the ostium and a portion of the coronary sinus adjacent to the ostium. The textured exterior surface can comprise either or both of a plurality of bumps and a plurality of ridges.

In some embodiments, the inner lumen is configured to receive a therapy device delivery catheter carrying a therapy device for deployment to a heart location. The therapy device can comprise a shunt device for deployment onto a left atrial wall.

In some implementations, a method of accessing a heart location can comprise providing a steerable sheath which includes an elongate tubular member, a circumferential balloon anchor circumferentially positioned around a distal portion of the elongate tubular member and a plurality of cords circumferentially distributed around the circumferential balloon anchor. The distal portion of the elongate tubular member can be introduced through an inferior vena cava or a superior vena cava, and into a right atrium. A distal end of the elongate tubular member can be inserted through an ostium of a coronary sinus into the coronary sinus from the right atrium, and the distal end can be positioned at a target location within the coronary sinus. The circumferential balloon anchor can be inflated and an inflated circumferential balloon anchor can be engaged with the plurality of cords to create corresponding circumferentially distributed indentations on the inflated circumferential balloon anchor. The inflated circumferential balloon anchor can be engaged with the coronary sinus while blood flow is permitted through the ostium past the inflated circumferential balloon anchor along a path defined at least in part by the circumferentially distributed indentations.

In some embodiments, engaging the coronary sinus comprises engaging the inflated circumferential balloon anchor with the ostium of the coronary sinus.

In some embodiments, the plurality of cords can be moved proximally along a longitudinal axis of the elongate tubular member, respective distal ends of the plurality of cords being coupled to corresponding locations on a distal balloon portion, where moving the plurality of cords compresses the inflated circumferential balloon anchor to provide the corresponding circumferentially distributed indentations on the inflated circumferential balloon anchor.

In some embodiments, a delivery catheter carrying a therapy device can be inserted into an inner lumen of the elongate tubular member. A distal end of the delivery catheter can be advanced from the distal end of the elongate tubular member for positioning at the target location. The delivery catheter can comprise a shunt delivery catheter carrying an atrial shunt device.

In some implementations, a steerable sheath can comprise an elongate tubular member which includes an inner lumen configured to receive a plurality of instruments, and a deformable helical rib anchor disposed around a distal portion of the elongate tubular member, the deformable helical rib anchor being configured to engage with a coronary sinus, and to permit blood flow through an ostium of the coronary sinus along a path defined at least in part by the deformable helical rib anchor while the deformable helical rib is positioned to engage with the coronary sinus.

In some embodiments, the deformable helical rib anchor is configured to be positioned to engage with both the ostium of the coronary sinus and a portion of the coronary sinus adjacent to the ostium.

In some embodiments, a height at which the deformable helical rib anchor extends from the distal portion of the elongate tubular member increases with increased distance from a distal end of the elongate tubular member. In some embodiments, a height at which the deformable helical rib anchor extends from the distal portion of the elongate tubular member is uniform along a dimension of the deformable helical rib anchor parallel with a longitudinal axis of the elongate tubular member.

In some embodiments, the inner lumen is configured to receive a therapy device delivery catheter carrying a therapy device for deployment to a heart location. The therapy device can comprise a shunt device for deployment onto a left atrial wall.

In some implementations, a steerable sheath can comprise an elongate tubular member which includes an inner lumen configured to receive a plurality of instruments, and a first expandable coil anchor disposed around a distal portion of the elongate tubular member, the first expandable coil being configured to engage with a coronary sinus and to permit blood flow through an ostium of the coronary sinus while the first expandable coil anchor is in an expanded state and positioned to engage with the coronary sinus.

In some embodiments, the first expandable coil is configured to be positioned to engage with the ostium of the coronary sinus.

In some embodiments, the steerable sheath further comprises a second expandable coil anchor positioned distally adjacent to the first expandable coil anchor, the second expandable coil anchor comprising a diameter smaller than that of the first expandable coil anchor, the second expandable coil anchor being configured to engage with a portion of the coronary ostium adjacent to the ostium when in an expanded state. The first expandable coil anchor and the second expandable coil anchor can be configured to permit blood flow through the ostium while the first expandable coil anchor and the second expandable coil anchor are positioned to engage with the ostium and the portion of the coronary sinus adjacent to the ostium.

In some embodiments, the inner lumen can be configured to receive a therapy device delivery catheter carrying a therapy device for deployment to a heart location. The therapy device can comprise a shunt device for deployment onto a left atrial wall.

In some implementations, a steerable sheath can comprise an elongate tubular member which includes an inner lumen configured to receive a plurality of instruments, and a partially circumferential ring anchor disposed partially circumferentially on a distal portion of the elongate tubular member, the partially circumferential ring anchor being configured to permit blood flow through an ostium of a coronary sinus while the partially circumferential ring anchor is positioned to engage with the coronary sinus.

In some embodiments, the partially circumferential ring anchor is configured to be positioned to engage with the ostium.

In some embodiments, the partially circumferential ring anchor comprises a proximal ring portion and a distal ring portion, the distal ring portion comprising a tapered longitudinal profile tapering toward a distal end of the ring, the partially circumferential ring anchor being configured to engage with the ostium and a portion of the coronary sinus adjacent to the ostium.

In some embodiments, the partially circumferential ring is disposed around less than 50% of a circumference of the distal portion of the elongate tubular member.

In some embodiments, the inner lumen is configured to receive a therapy device delivery catheter carrying a therapy device for deployment to a heart location. The therapy device can comprise a shunt device for deployment onto a left atrial wall.

In some implementations, a method of accessing a heart location can comprise providing a steerable sheath which includes an elongate tubular member and an anchor positioned on a distal portion of the elongate tubular member. The distal portion of the elongate tubular member can be introduced through an inferior vena cava or a superior vena cava, and into a right atrium. A distal end of the elongate tubular member can be inserted through an ostium of a coronary sinus into the coronary sinus from the right atrium, and the distal end can be positioned at a target location within the coronary sinus. The anchor can be engaged with the coronary sinus while blood flow is permitted through the ostium past the anchor.

In some embodiments, engaging the coronary sinus comprises engaging the ostium of the coronary sinus with the anchor.

In some embodiments, a delivery catheter carrying a therapy device can be inserted into an inner lumen of the elongate tubular member, and a distal end of the delivery catheter can be advanced from the distal end of the elongate tubular member for positioning at the target location. The delivery catheter carrying a therapy device can comprise a shunt delivery catheter carrying an atrial shunt device For purposes of summarizing the disclosure, certain aspects, advantages and novel features have been described herein. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

Various embodiments are depicted in the accompanying drawings for illustrative purposes and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements. However, it should be understood that the use of similar reference numbers in connection with multiple drawings does not necessarily imply similarity between respective embodiments associated therewith. Furthermore, it should be understood that the features of the respective drawings are not necessarily drawn to scale, and the illustrated sizes thereof are presented for the purpose of illustration of inventive aspects thereof. Generally, certain of the illustrated features may be relatively smaller than as illustrated in some embodiments or configurations.

FIG. 16 is a flow diagram of an example of a procedure for deploying a steerable sheath into the coronary sinus.

FIG. 17 is a flow diagram of an example of a procedure for deploying a steerable sheath comprising a circumferential balloon anchor into the coronary sinus.

DETAILED DESCRIPTION

Figure 1:
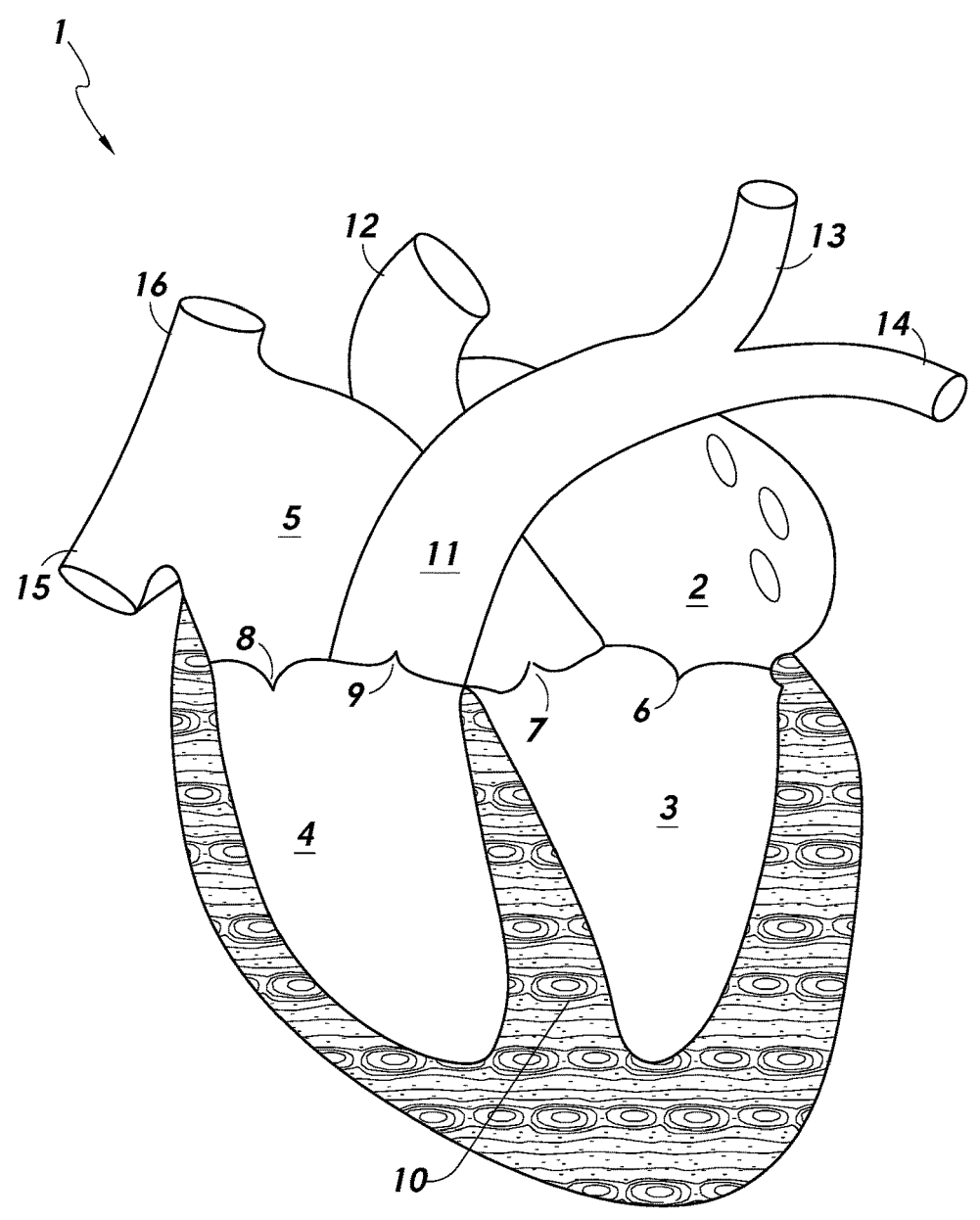
FIG. 1 is a cross-sectional view of a human heart.

The headings provided herein are for convenience only and do not necessarily affect the scope or meaning of the claimed invention.

The present disclosure relates to systems, devices, and methods for providing reliable positioning of delivery sheaths into the coronary sinus from the right atrium via the coronary sinus ostium. The steerable sheaths can comprise an anchor configured to engage with the coronary sinus ostium, or both the coronary sinus ostium and a portion of the coronary sinus adjacent to the ostium, for providing stable transcatheter access into the coronary sinus.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Certain standard anatomical terms of location are used herein to refer to the anatomy of animals, and namely humans, with respect to the preferred embodiments. Although certain spatially relative terms, such as "outer," "inner," "upper," "lower," "below," "above," "vertical," "horizontal," "top," "bottom," and similar terms, are used herein to describe a spatial relationship of one device/element or anatomical structure to another device/element or anatomical structure, it is understood that these terms are used herein for ease of description to describe the positional relationship between element(s)/structures(s), as illustrated in the drawings. It should be understood that spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

Various features of a heart 1 are described with reference to FIG. 1 to assist in understanding the present disclosure. The heart 1 includes four chambers, namely the left atrium 2, the left ventricle 3, the right ventricle 4, and the right atrium 5. A wall of muscle, referred to as the septum 10, separates the left atrium 2 and right atrium 5, and the left ventricle 3 and right ventricle 4. Blood flow through the heart 1 is at least partially controlled by four valves, the mitral valve 6, aortic valve 7, tricuspid valve 8, and pulmonary valve 9. The mitral valve 6 separates the left atrium 2 and the left ventricle 3 and controls blood flow therebetween. The aortic valve 7 separates and controls blood flow between the left ventricle 3 and the aorta 12. The tricuspid valve 8 separates the right atrium 5 and the right ventricle 4 and controls blood flow therebetween. The pulmonary valve 9 separates the right ventricle 4 and the pulmonary artery 11, controlling blood flow therebetween.

In a healthy heart, the heart valves can properly open and close in response to a pressure gradient present during various stages of the cardiac cycle (e.g., relaxation and contraction) to at least partially control the flow of blood to a respective region of the heart and/or to blood vessels. Deoxygenated blood arriving from the rest of the body generally flows into the right side of the heart for transport to the lungs, and oxygenated blood from the lungs generally flows into the left side of the heart for transport to the rest of the body. During ventricular diastole, deoxygenated blood arrive in the right atrium 5 from the inferior vena cava 15 and superior vena cava 16 to flow into the right ventricle 4, and oxygenated blood arrive in the left atrium 2 from the pulmonary veins to flow into the left ventricle 3. During ventricular systole, deoxygenated blood from the right ventricle 4 can flow into the pulmonary artery 11 for transport to the lungs (e.g., via the left 14 and right 13 pulmonary arteries), and oxygenated blood can flow from the left ventricle 3 to the aorta 12 for transport to the rest of the body.

A number of conditions can contribute to a higher than normal pressure in the left atrium. Dysfunction of the mitral valve can contribute to elevated left atrial pressure. Conditions such as mitral valve regurgitation and/or stenosis may result in difficulty in pumping blood from the left atrium to the left ventricle, contributing to elevated pressure in the left atrium. Valve stenosis can cause a valve to become narrowed or obstructed. Mitral valve stenosis can restrict blood flow from the left atrium to the left ventricle. Valve regurgitation occurs when a valve does not close properly. For example, regurgitation can occur due to improper coaptation of the valve leaflets. Mitral valve regurgitation can result in blood flow leakage back into the left atrium 2 from the left ventricle 3 when the left ventricle 3 contracts. Restricted flow of blood from the left atrium 2 into the left ventricle 3, and blood flow leakage from the left ventricle 3 back into the left atrium 2 can both contribute to elevated atrial pressure. Dysfunction in the left ventricle 3 can also contribute to elevated left atrial pressure. Elevated left atrial pressure may lead to left atrial enlargement, producing symptoms such as shortness of breath during exertion, fatigue, chest pain, fainting, abnormal heartbeat, and swelling of the legs and feet.

Figure 2:
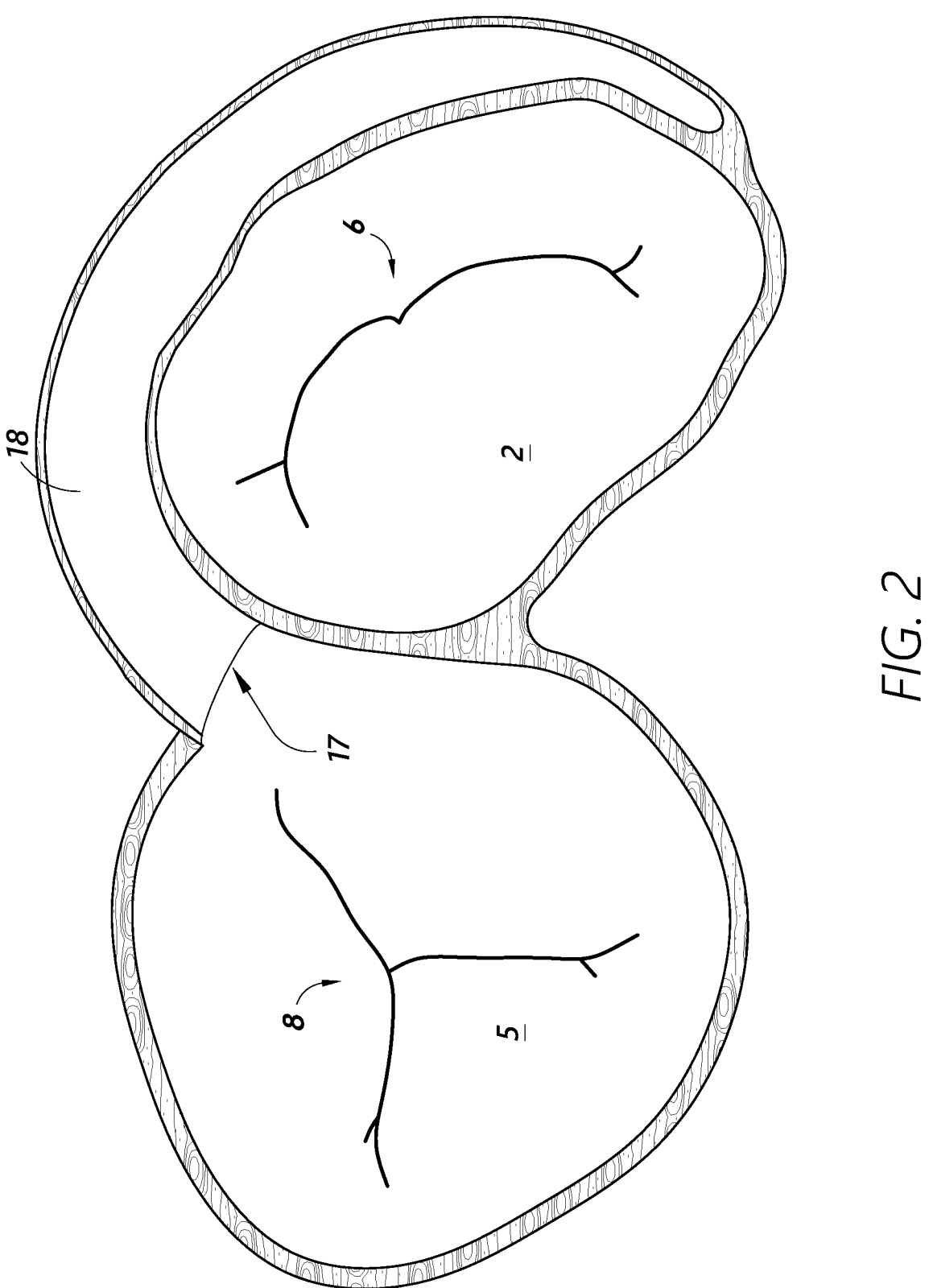
FIG. 2 is another cross-sectional view of the human heart.

FIG. 2 is another view of the heart 1 and shows the coronary sinus 18 around the left atrium 2. To alleviate elevated left atrial pressure, a conduit can be provided to allow blood flow from the left atrium 2 into a portion of the heart with lower pressure, such as the coronary sinus 18. A conduit can be formed on the wall of the left atrium 2 adjacent to the coronary sinus 18 to allow blood flow from the left atrium 2 into the coronary sinus 18. The coronary sinus 18 receives blood from coronary veins and empties into the right atrium 5. Blood diverted into the coronary sinus 18 from the left atrium 2 can then be delivered into the right atrium 5. A shunt device can be positioned at a location on the left atrial wall, such as at a location on the left atrial wall which is accessible from the coronary sinus 18, to form a blood flow pathway from the left atrium 2 into the coronary sinus 18. Access into the coronary sinus 18 can comprise navigating into the right atrium 5 and entering through the coronary sinus ostium 17.

Figure 3B:
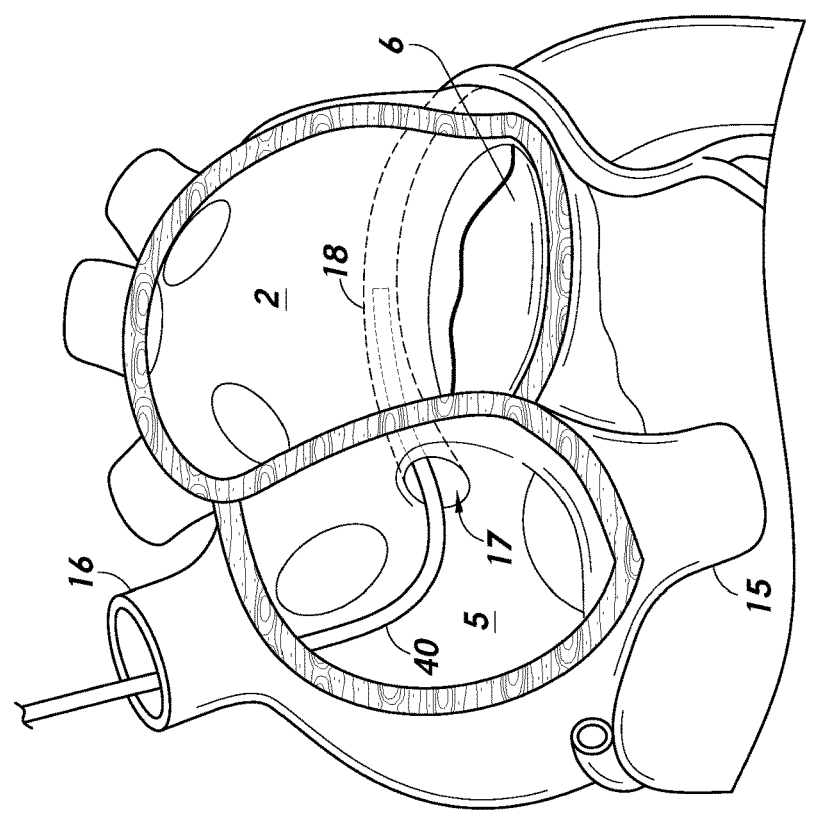
FIGS. 3A and 3B show examples of pathways for accessing the coronary sinus from the right atrium.
Figure 3A:
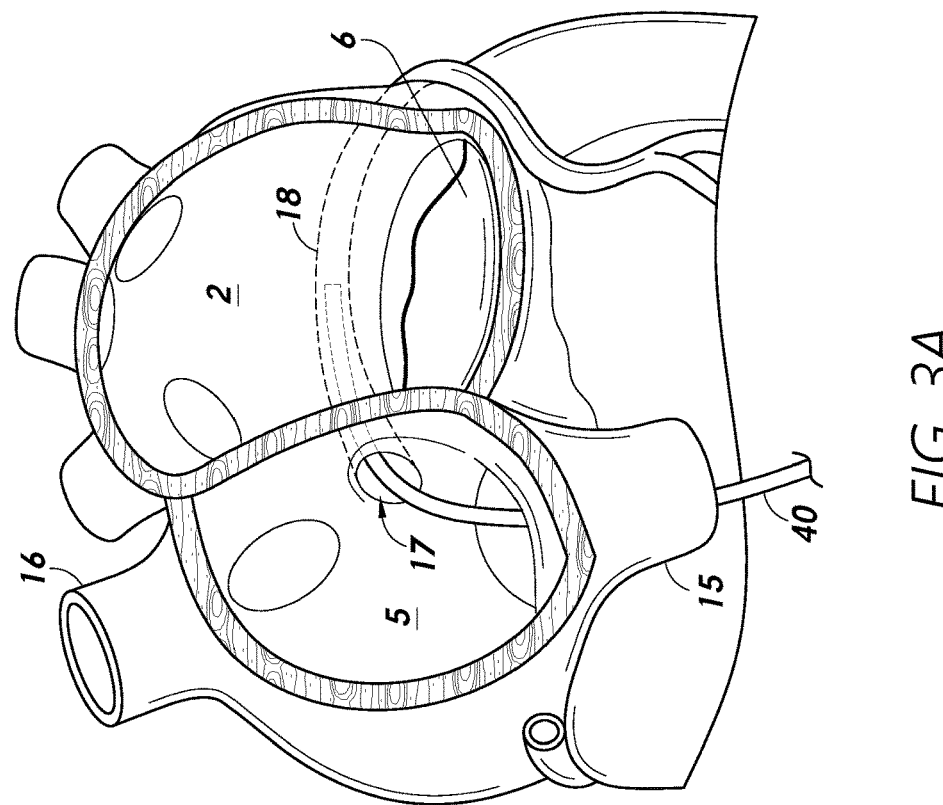

FIGS. 3A and 3B show examples of pathways for accessing the coronary sinus 18 through the right atrium 5 to deliver a shunt or other implant device to a portion of the left atrial wall. In FIG. 3A, a steerable sheath 40 is shown as being inserted through the inferior vena cava 15 and into the right atrium 5. For example, the steerable sheath 40 can be introduced through the femoral vein, and then inserted through the inferior vena cava 15. The steerable sheath 40 can then be advanced from the right atrium 5 through the coronary sinus ostium 17 and into the coronary sinus 18.

In FIG. 3B, the steerable sheath 40 is shown as being inserted through the superior vena cava 16 and into the right atrium 5. The steerable sheath 40 can be introduced through the subclavian vein or jugular vein, and then inserted through the superior vena cava 16. The steerable sheath 40 can be positioned from the right atrium 5 through the coronary sinus ostium 17 and into the coronary sinus 18.

As shown in both FIGS. 3A and 3B, the steerable sheath 40 can be bent when positioned from the inferior vena cava 15 or the superior vena cava 16 into the right atrium 5 and from the right atrium 5 through the coronary sinus ostium 17. This curvature in the steerable sheath 40 can render stable positioning of the steerable sheath 40 difficult when moving instrumentation through an inner lumen of the steerable sheath 40 to position instrumentation within the coronary sinus 18. Advancing and/or retracting instrumentation through the steerable sheath 40, and/or rigidity of the steerable sheath 40, may inadvertently move the steerable sheath 40 and dislodge the steerable sheath 40 from its desired position. Movement of instrumentation within the steerable sheath 40 can push a distal end of the steerable sheath 40 positioned within the coronary sinus 18 back toward the coronary sinus ostium 17.

In some embodiments, the present disclosure relates to devices, systems and/or methods for providing stable transcatheter access into the coronary sinus from the right atrium via the coronary sinus ostium. Described herein are delivery sheaths, including steerable sheaths, for positioning into the coronary sinus, the steerable sheaths comprising an anchor configured to engage with the coronary sinus ostium, or both the coronary sinus ostium and a portion of the coronary sinus adjacent to the ostium. The anchor can be on a distal portion of an elongate tubular member of the steerable sheath, a distal end of the steerable sheath being configured to be positioned within the coronary sinus for accessing the left atrial wall. The anchor can allow stable positioning of the distal end within the coronary sinus to facilitate reliable delivery of one or more medical implant devices and/or therapies to a target tissue site on the left atrial wall.

As described in further detail herein, an elongate tubular member of a steerable sheath can be bent when positioned through the coronary sinus ostium from the right atrium. The steerable sheath can be inserted into the right atrium through the inferior vena cava or superior vena cava. The bend or curvature in the elongate tubular member can present difficulties in maintaining a stable and secure position within the coronary sinus. Insertion and/or retraction of instrumentation through the elongate tubular member, such as to deliver implant devices and/or therapies to the left atrial wall, can cause undesired movement of the distal portion of the elongate tubular member. The distal portion may be pushed back towards the right atrium, dislodging the elongate tubular member from its desired location within the coronary sinus.

Engaging an anchor with the coronary sinus ostium, or with both the coronary sinus ostium and an adjacent portion of the coronary sinus, can facilitate docking of the elongate tubular member against the coronary sinus ostium, or the coronary sinus ostium and an adjacent portion. Force can be exerted upon the elongate tubular member to maintain the distal portion of the elongate tubular member at its desired position within the coronary sinus. Engaging the anchor with the coronary sinus ostium, or the coronary sinus ostium and an adjacent portion, can prevent over insertion of the elongate tubular member into the coronary sinus, while reducing or avoiding movement of the elongate tubular member back towards the right atrium. The anchor can provide secure positioning of the elongate tubular member within the coronary sinus such that desired therapy device implants and/or therapeutic procedures can be delivered thereto. Engaging the anchor with the coronary sinus ostium can provide improved stability and/or reduce or prevent damage to the coronary sinus, such as compared to steerable sheaths comprising anchors for engaging only with portions within the coronary sinus.

An anchor can be positioned on a distal portion of an elongate tubular member, spaced from or at a distal end of the elongate tubular member. The anchor can comprise a shape configured to engage with the coronary sinus ostium, or the coronary sinus ostium and an adjacent portion. A cross-sectional size of the coronary sinus decreases along a direction extending into the coronary sinus and away from the ostium. In some embodiments, at least a portion of the anchor can comprise a taper configured to engage with the coronary sinus ostium and an adjacent portion of the coronary sinus. For example, a distal portion of the anchor can have a longitudinal profile comprising a taper toward a distal end of the anchor, the longitudinal profile extending along a direction parallel or substantially parallel to a longitudinal axis of the elongate tubular member. In some embodiments, the tapered distal portion can comprise a curvature, including a convex curvature. In some embodiments, an anchor can comprise a textured exterior surface configured to provide desired engagement with the coronary sinus ostium and/or an adjacent portion of the coronary sinus.

The anchor can be configured to be in engagement with the coronary sinus ostium and an adjacent portion of the coronary sinus, while permitting blood flow through the ostium past the anchor. Permitting blood flow through the ostium can advantageously allow performance of delivery procedures while a heart is beating, providing a lower risk of complications, shorter hospital stay and/or quicker recovery for the patient. For example, the anchor can be configured so as not to occlude the ostium. In some embodiments, the anchor can comprise any one of a partially circumferential balloon anchor, a circumferential balloon anchor comprising longitudinal indentations formed thereon, a helical rib anchor, a coil anchor, a partially circumferential ring anchor, and a suction anchor. As used herein, a partially circumferential anchor can refer to any anchor configured to be positioned on, disposed around and/or extending from, any partial portion of the circumference of a distal portion of an elongate tubular member, and where the anchor does not circumscribe the distal portion.

Although the description herein is made primarily with reference to positioning sheaths from the right atrium into the coronary sinus, it will be understood that the description can refer or generally apply to positioning of sheaths from a first body chamber or lumen into a second body chamber or lumen, where the sheaths may be bent when positioned from the first body chamber or lumen into the second body chamber or lumen. A body chamber or lumen can refer to any one of a number of fluid channels, blood vessels, and/or organ chambers (e.g., heart chambers). Additionally, reference herein to "sheaths", "delivery sheaths" and/or "steerable sheaths" can refer or apply generally to any type of elongate tubular delivery device comprising an inner lumen configured to slidably receive instrumentation, such as for positioning within an atrium or coronary sinus. "Sheaths", "delivery sheaths" and/or "steerable sheaths" can include, for example, delivery catheters and/or cannulas. It will be understood that other types of medical implant devices and/or procedures can be delivered to the coronary sinus using a steerable sheath as described herein, including for example ablation procedures, drug delivery and/or placement of coronary sinus leads.

Figure 4:
FIG. 4 is a schematic diagram of an example of a delivery system comprising a steerable sheath and a delivery catheter received within an inner lumen of the steerable sheath.

FIG. 4 is a schematic diagram of a delivery system 50 which comprises a steerable sheath 100 that includes an anchor 140. The steerable sheath 100 can comprise an elongate tubular member 110 having a proximal portion 112 and a distal portion 114. The anchor 140 can be on the distal portion 114 of the elongate tubular member 110. Various examples of the anchor 140 are described herein. For example, the anchor 140 can comprise any one of a partially circumferential balloon anchor, a circumferential balloon anchor having longitudinal indentations formed thereon, a helical rib anchor, a coil anchor, a partially circumferential ring anchor, and a suction anchor, as described herein.

The steerable sheath 100 can be configured to facilitate positioning of instrumentation at a target site within various body chambers or lumens. In some embodiments, the steerable sheath 100 can be configured to facilitate positioning of instrumentation at a target site within the coronary sinus, including a target tissue site on the left atrial wall accessible from within the coronary sinus. A delivery catheter 60 can be slidably received within an inner lumen of the elongate tubular member 110. A distal end 116 of the elongate tubular member 110 can be placed at or proximate to a target tissue site, including a target site in the coronary sinus. A distal end 62 of the delivery catheter 60 can be extended from the distal end 116 of the elongate tubular member 110 to position the distal end 62 of the delivery catheter 60 at or proximate to the target tissue site, such as to deploy one or more therapy devices to the target tissue site. In some embodiments, the delivery catheter 60 can be configured to carry one or more therapy devices for treatment of elevated left atrial pressure, such as an atrial shunt device. In some embodiments, the distal end 62 of the delivery catheter 60 can be positioned at or adjacent to a target site on the left atrial wall so as to facilitate deployment of an atrial shunt device onto the left atrial wall. It will be understood that other instrumentation can be received within the inner lumen, in addition to or instead of the delivery catheter 60.

In some embodiments, the steerable sheath 100 can be used to access the left atrial wall from within the coronary sinus by entering the coronary sinus from the right atrium through the coronary sinus ostium. As described herein, access into the right atrium can be made through the inferior vena cava or the superior vena cava. For example, the distal portion 114 of the elongate tubular member 110 can be configured to be advanced into the right atrium from the inferior vena cava or the superior vena cava. The distal portion 114 can then be inserted through the coronary sinus ostium from the right atrium, and into the coronary sinus. In some embodiments, the anchor 140 on the distal portion 114 can be configured to engage with the coronary sinus ostium. In some embodiments, the anchor 140 can be configured to engage with the coronary sinus ostium and a portion of the coronary sinus adjacent to the ostium. The anchor 140 can comprise a shape and/or size to provide desired engagement with the coronary sinus ostium, or the coronary sinus ostium and a portion of the coronary sinus adjacent to the ostium, while permitting flow of blood through the ostium past the anchor 140.

The anchor 140 can be at or a distance away from the distal end 116 of the elongate tubular member 110. In some embodiments, the anchor 140, such as a distal end of the anchor 140, can be at a distance of less than about 5 centimeters (cm) from the distal end 116 of the elongate tubular member 110, or less than about 4 cm, about 3 cm, about 2 cm, or about 1 cm. In some embodiments, the anchor 140 can be about 1 cm, about 2 cm, about 3 cm, or about 4 cm, from the distal end 116. In some embodiments, the anchor 140 can be at the distal end 116.

In some embodiments, the anchor 140 can comprise one or more radiopaque markers 140*a* to facilitate visualization of the positioning of the anchor 140, the distal portion 114 and/or the distal end 116 of the elongate tubular member 110. For example, the radiopaque markers 140*a* can facilitate desired positioning of the anchor 140 at the coronary sinus ostium. In some embodiments, the one or more radiopaque markers 140*a* can provide visualization of a shape, orientation, and/or location of the anchor 140 to facilitate correct positioning of the anchor 140 at the coronary sinus ostium, including visualization of a desired deformation of the anchor 140. For example, visualization of the deformation of a partially circumferential balloon anchor, a circumferential balloon anchor, and/or a helical rib anchor can be used to determine whether desired contact is made with the coronary sinus ostium and/or an adjacent portion of the coronary sinus.

As described herein, the anchor 140 can be configured to engage with the coronary sinus ostium, or the coronary sinus ostium and a portion of the coronary sinus adjacent to the ostium, to reduce or prevent undesired movement of the elongate tubular member 110. The anchor 140 can be configured to prevent dislodging of the elongate tubular member 110 from its desired position within the coronary sinus, such as when instrumentation is inserted and/or retracted through the inner lumen of the elongate tubular member 110. Reliable positioning of the elongate tubular member 110 within the coronary sinus can facilitate delivery of therapy device implants and/or application of therapeutic treatments to target sites accessible from within the coronary sinus, including target sites on the left atrial wall.

The anchor 140 can be configured to be in engagement with the coronary sinus ostium, or the coronary sinus ostium and an adjacent portion of the coronary sinus, while permitting blood flow through the ostium past the anchor 140. The anchor 140 can be configured so as not to occlude the ostium. Permitting blood flow through the ostium can have various advantages, including performance of procedures while a heart is beating. Beating heart surgeries can provide a lower risk of complications, shorter hospital stay and/or quicker recovery for the patient.

In some embodiments, the anchor 140 can be an integral part of the elongate tubular member 110. In some embodiments, the anchor 140 can be separable from the elongate tubular member 110. For example, the anchor 140 can be a separate component associated with the elongate tubular member 110 where the anchor 140 is configured to be coupled to the distal portion 114 of the elongate tubular member 110. The anchor 140 can be selected for coupling to the elongate tubular member 110. For example, a desired anchor can be selected for positioning onto the elongate tubular member 110 based on a number of factors, including a size and/or shape of the coronary sinus ostium and/or a distance from the ostium of the target site within the coronary sinus.

Figure 5:
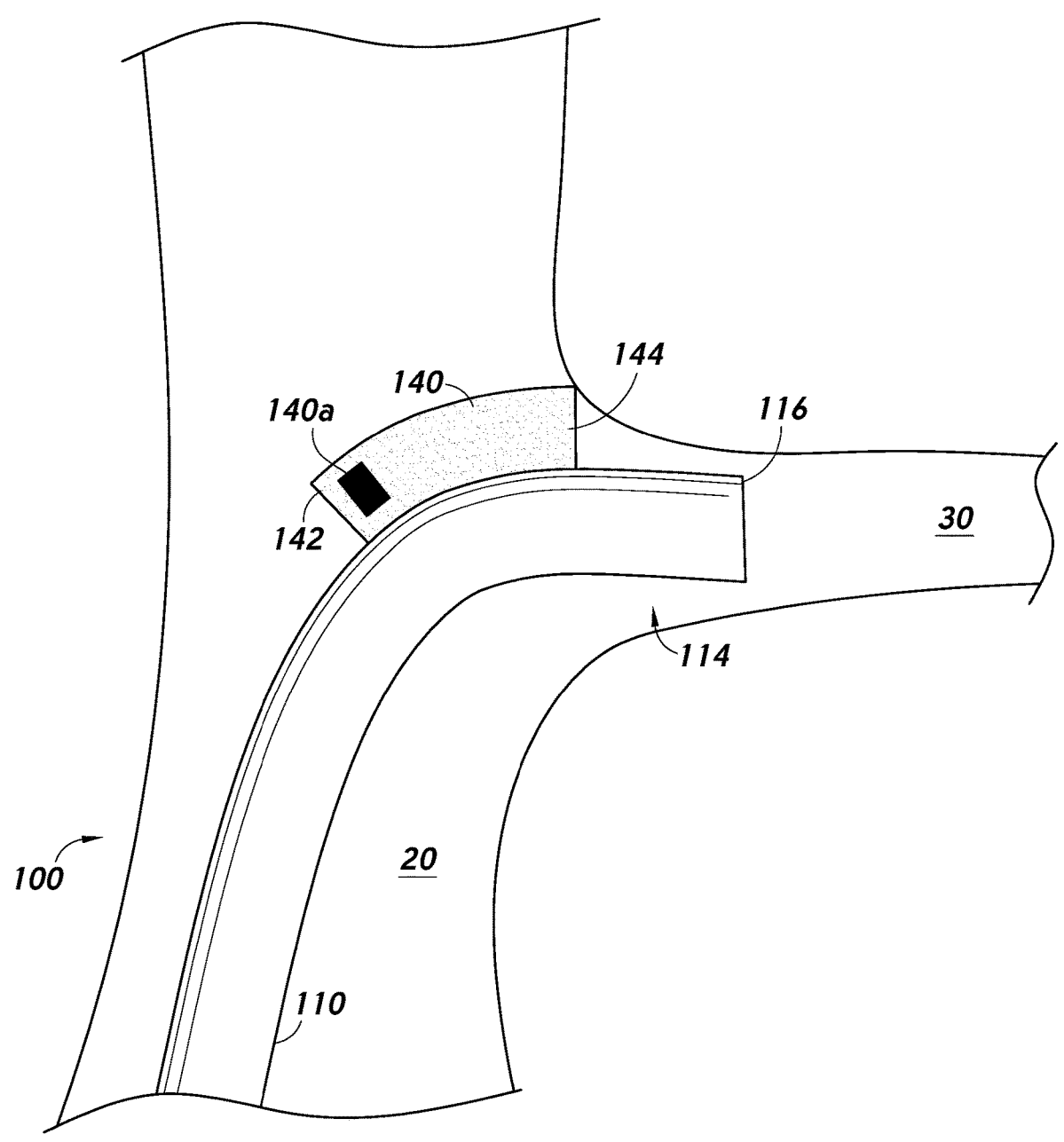
FIG. 5 is a schematic diagram of the steerable sheath of FIG. 4 positioned from a first body chamber or lumen into a second body chamber or lumen.

FIG. 5 is a schematic diagram showing the steerable sheath 100 positioned from a first body chamber or lumen 20 into a second body chamber or lumen 30. The first body chamber or lumen 20 and the second body chamber or lumen 30 can be any one of a number of fluid channels, blood vessels, and/or organ chambers. In some embodiments, the first body chamber or lumen 20 can be the right atrium and the second body chamber or lumen 30 can be the coronary sinus.

The distal portion 114 of the elongate tubular member 110 can have a bend while positioned from the first body chamber or lumen 20 into the second body chamber or lumen 30. The anchor 140 can be positioned at the opening of the second body chamber or lumen 30. The distal end 116 of the elongate tubular member 110 can extend into the second body chamber or lumen 30 while the anchor 140 is positioned at the opening of the second body chamber or lumen 30. As described herein, the anchor 140 can comprise one or more radiopaque markers 140*a* to facilitate visualization of the positioning of the anchor 140, the distal portion 114 and/or the distal end 116 of the elongate tubular member 110.

In some embodiments, one or more portions of the anchor 140 can be configured to engage with the opening of the second body chamber or lumen 30. In some embodiments, one or more portions of the anchor 140 can be configured to engage with both the opening of the second body chamber or lumen 30 and a portion of the second body chamber or lumen 30 adjacent to the opening. For example, the anchor 140 can have a proximal portion 142 and a distal portion 144, where the distal portion 144 of the anchor 140 can be configured to engage with the opening of the second body chamber or lumen 30. In some embodiments, the distal portion 144 of the anchor 140 can be configured to engage with both the opening of the second body chamber or lumen 30 and an adjacent portion of the second body chamber or lumen 30. It will be understood that although FIG. 5 shows the anchor 140 as being positioned outside of the second body chamber or lumen 30, the anchor 140 can be positioned at least partially within the second body chamber or lumen 30.

Engaging the anchor 140 with the opening of the second body chamber or lumen 30, or with both the opening of the second body chamber or lumen 30 and an adjacent portion of the second body chamber or lumen 30, can facilitate docking of the elongate tubular member 110 against the opening of the second body chamber or lumen 30, or both the opening of the second body chamber or lumen 30 and an adjacent portion of the second body chamber or lumen 30. As such, over insertion of the elongate tubular member 110 into the second body chamber or lumen 30, and/or undesired movement of the elongate tubular member 110, can be prevented or reduced.

Figure 6:
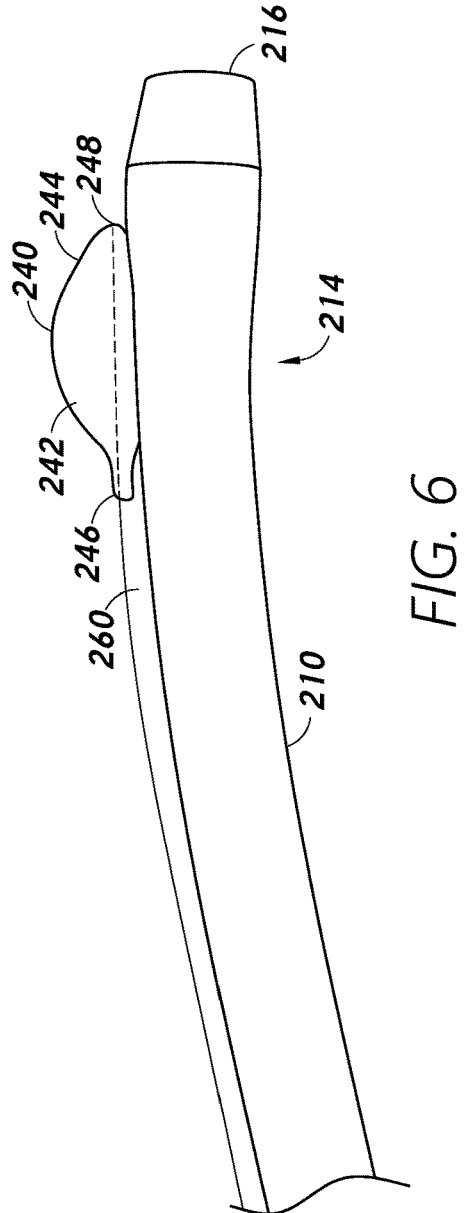
FIG. 6 is a schematic diagram of a side view of an example of a steerable sheath comprising a partially circumferential balloon anchor.

FIG. 6 is a side view of an example of a steerable sheath 200 comprising a partially circumferential balloon anchor 240. The steerable sheath 200 can comprise an elongate tubular member 210 and the partially circumferential balloon anchor 240 can be positioned around only a portion of a circumference of a distal portion 214 of the tubular member 210. As used herein, a partially circumferential balloon anchor can refer to any balloon anchor configured to be positioned on, disposed around and/or extending from, any partial portion of the circumference of the distal portion 214, and where the balloon anchor does not circumscribe the distal portion 214.

In some embodiments, the partially circumferential balloon anchor 240 can be inflatable. For example, the steerable sheath 200 can comprise an inflation and deflation lumen 260 extending along at least a portion of the elongate tubular member 210, the inflation and deflation lumen 260 being configured to allow inflation or deflation of the partially circumferential balloon anchor 240. The partially circumferential balloon anchor 240, when in an inflated state, can be configured to contact and engage with the coronary sinus ostium and a portion of the coronary sinus adjacent to the ostium, so as to facilitate reliable positioning of the elongate tubular member 210 within the coronary sinus.

The partially circumferential balloon anchor 240 can comprise a proximal end 246 and a distal end 248. The partially circumferential balloon anchor 240 can be positioned on the distal portion 214 of the elongate tubular member 210 such that both the proximal end 246 and the distal end 248 are on the distal portion 214. In some embodiments, the partially circumferential balloon anchor 240 can be positioned a distance away from a distal end 216 of the elongate tubular member 210. For example, the distal end 248 of the circumferential balloon anchor 240 can be spaced from the distal end 216 of the elongate tubular member 210 such that the circumferential balloon anchor 240 can be positioned at the coronary sinus ostium, while the distal end 216 of the elongate tubular member 210 can be positioned further within the coronary sinus, such as at or proximate to a target tissue location. In some embodiments, the distal end 248 of the partially circumferential balloon anchor 240 can be at the distal end 216 of the elongate tubular member 210.

In some embodiments, the partially circumferential balloon anchor 240 can be inflatable. In the inflated state, the partially circumferential balloon anchor 240 can comprise a shape configured to engage the coronary sinus ostium and a portion of the coronary sinus adjacent to the ostium. As described herein, a cross-sectional size of the coronary sinus decreases along a direction extending into the coronary sinus and away from the ostium. A distal portion 244 of the partially circumferential balloon anchor 240 can be configured to engage with the coronary sinus ostium and an adjacent portion of the coronary sinus. For example, the distal portion 244 can have a longitudinal profile comprising a taper toward the distal end 248 of the partially circumferential balloon anchor 240, the longitudinal profile extending along a direction parallel or substantially parallel to a longitudinal axis of the elongate tubular member 210. The taper of the longitudinal profile can be configured to facilitate desired engagement of the distal portion 244 with the coronary sinus ostium and a portion of the coronary sinus adjacent to the ostium. In some embodiments, the tapered distal portion 244 can comprise a curvature, such as a convex curvature. For example, the longitudinal profile of the distal portion 244 can comprise a curved taper, such as a curved convex taper, which tapers towards the distal end 248 of the partially circumferential balloon anchor 240. The longitudinal profile of the distal portion 244 can be selected to provide secure engagement of the partially circumferential balloon anchor 240 with the coronary sinus ostium and an adjacent portion of the coronary sinus.

In some embodiments, a proximal portion 242 of the partially circumferential balloon anchor 240 can comprise a shape configured to facilitate movement of the partially circumferential balloon anchor 240 through anatomical pathways, including during retraction of the partially circumferential balloon anchor 240. For example, the proximal portion 242 of the partially circumferential balloon anchor 240 can have a longitudinal profile comprising a taper toward the proximal end 246 of the partially circumferential balloon anchor 240, the longitudinal profile extending along a direction parallel or substantially parallel to a longitudinal axis of the elongate tubular member 210. The longitudinal profile of the proximal portion 242 can comprise a curved taper, such as a curved convex taper, which tapers towards the proximal end 246 of the partially circumferential balloon anchor 240. In some embodiments, the partially circumferential balloon anchor 240 can have a maximum cross-sectional size at or around a mid-portion of the anchor 240, and a longitudinal profile of both the proximal portion 242 and distal portion 244 comprising a taper, including a curved convex taper, from or around the mid-portion of the anchor 240 toward the proximal end 246 and the distal tend 248, respectively.

In some embodiments, the partially circumferential balloon anchor 240 can have a length of up to about 10 millimeters (mm), including about 1 mm to about 9 mm, about 2 mm to about 8 mm, or about 3 mm to about 7 mm. In some embodiments, the partially circumferential balloon anchor 240 has a length of about 10 mm. In some embodiments, a width of the partially circumferential balloon anchor 240 can be about 1 mm to about 10 mm. In some embodiments, the partially circumferential balloon anchor 240 can have a width which varies from about 1 mm to about 10 mm. For example, the distal portion 244 can taper from a width of about 10 mm to a width of about 1 mm at the distal end 248, including from about 9 mm down to about 1 mm, about 8 mm down to about 1 mm, about 9 mm down to about 2 mm, about 8 mm down to about 2 mm, about 7 mm down to about 3 mm, or about 6 mm down to about 4 mm. In some embodiments, the proximal portion 242 can have the same or similar taper in width.

In some embodiments, the partially circumferential balloon anchor 240 can be kept in a deflated state during at least a part of its insertion to and/or retraction from the coronary sinus ostium. In some embodiments, the partially circumferential balloon anchor 240 can assume an inflated state after the distal portion 214 of the elongate tubular member 210 is positioned at a desired location. For example, after the distal end 216 of the elongate tubular member 210 is positioned at or adjacent to the target tissue site and the partially circumferential balloon anchor 240 is at the coronary sinus ostium, the partially circumferential balloon anchor 240 can be inflated. The partially circumferential balloon anchor 240 can be inflated until desired engagement with the coronary sinus ostium and an adjacent portion of the coronary sinus is achieved. In some embodiments, the partially circumferential balloon anchor 240 can be inflated before the distal portion 214 of the elongate tubular member 210 is positioned at the desired location. For example, the partially circumferential balloon anchor 240 can assume an inflated state after being positioned within the right atrium but before being positioned to engage the coronary sinus ostium and an adjacent portion of the coronary sinus. In some embodiments, the partially circumferential balloon anchor 240 can be expanded both before and after being positioned at a target location. For example, the partially circumferential balloon anchor 240 can assume a partially inflated state while in the right atrium, and further inflation can be performed after being positioned to engage the coronary sinus ostium. In some embodiments, a degree of inflation of the partially circumferential balloon anchor 240 can be adjusted during a procedure in response to a size of a coronary sinus ostium and an adjacent portion of the coronary sinus. In some embodiments, the partially circumferential balloon anchor 240 can be deflated for retraction.

Figure 7:
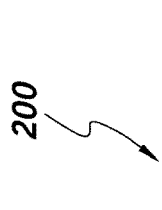
FIG. 7 is a schematic diagram of a view of the distal portion of the steerable sheath of FIG. 6.
Figure 7:
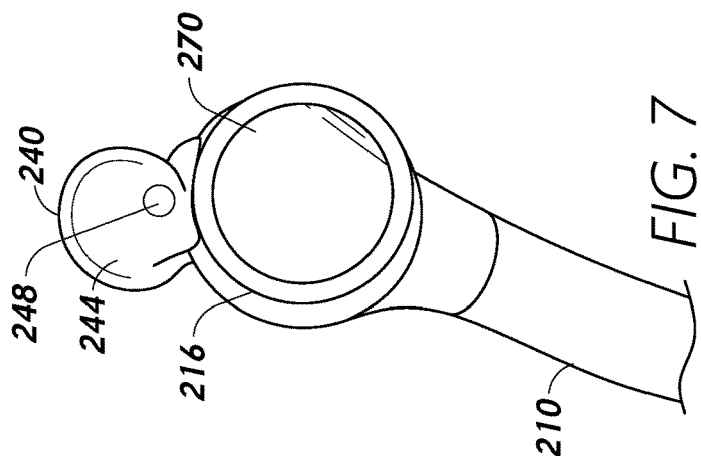

FIG. 7 is a view of the distal portion 214 of the elongate tubular member 210. The distal end 248 and the distal portion 244 of the partially circumferential balloon anchor 240 is shown. As shown in FIG. 7, the partially circumferential balloon anchor 240 can be positioned around only a portion of the circumference of the distal portion 214. Having the partially circumferential balloon anchor 240 only around a portion of the circumference of the distal portion 214 can facilitate blood flow through the coronary sinus ostium and past the partially circumferential balloon anchor 240 while the partially circumferential balloon anchor 240 is positioned at and in engagement with the coronary sinus ostium and an adjacent portion of the coronary sinus. The partially circumferential balloon anchor 240 can provide sufficient contact with the coronary sinus ostium and an adjacent portion of the coronary sinus while allowing desired area around the steerable sheath 200 at the coronary sinus ostium such that sufficient blood flow can pass therethrough. In some embodiments, the partially circumferential balloon anchor 240 can be positioned around less than about 50% of the circumference of the distal portion 214 of the elongate tubular member 210, or less than about 40%, less than about 30%, less than about 25%, or less than about 20%.

As shown in FIG. 7, an inner lumen 270 of the elongate tubular member 210 extends to the distal end 216 of the elongate tubular member 210. The inner lumen 270 can be configured to receive various instrumentation for delivering one or more therapy devices to a target tissue location.

Figure 8:
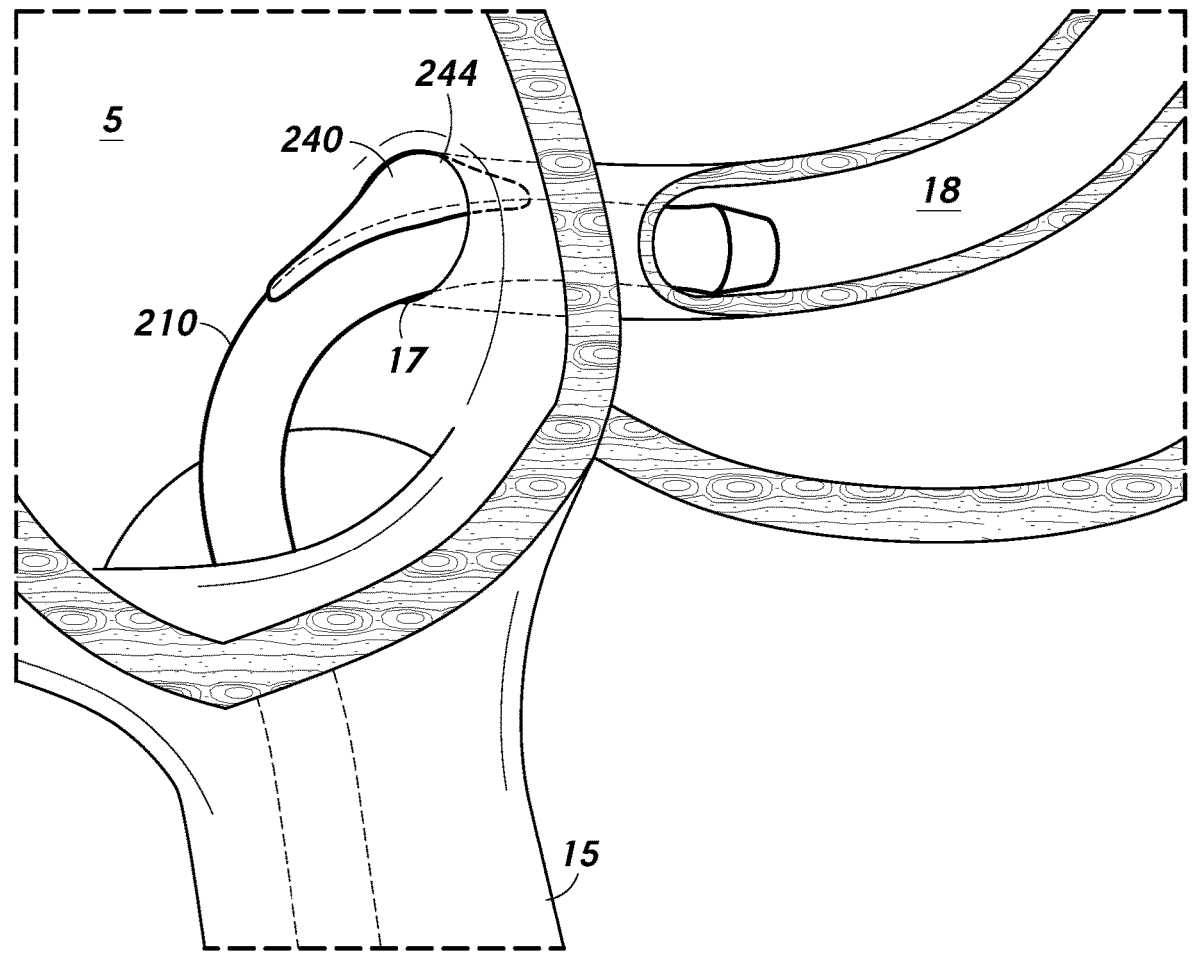
FIG. 8 shows the steerable sheath of FIG. 6 positioned for accessing a target location within the coronary sinus.

FIG. 8 shows the steerable sheath 200 in a position for accessing a target location within the coronary sinus 18. The elongate tubular member 210 can be advanced through the inferior vena cava 15, positioned into the right atrium 5, and inserted through the coronary sinus ostium 17 into the coronary sinus 18. The distal end (not shown) of the elongate tubular member 210 can be positioned within the coronary sinus 18. The partially circumferential balloon anchor 240 can be positioned against the coronary sinus ostium 17 such that the distal portion 244 engages the coronary sinus ostium 17 and a portion of the coronary sinus 18 adjacent to the ostium 17. The distal end of the partially circumferential balloon anchor 240 can be positioned within the coronary sinus 18. The tapering of the longitudinal profile of the distal portion 244 can facilitate stable and/or reliable engagement of the partially circumferential balloon anchor 240 with the coronary sinus ostium 17 and an adjacent portion of the coronary sinus 18.

Figure 9:
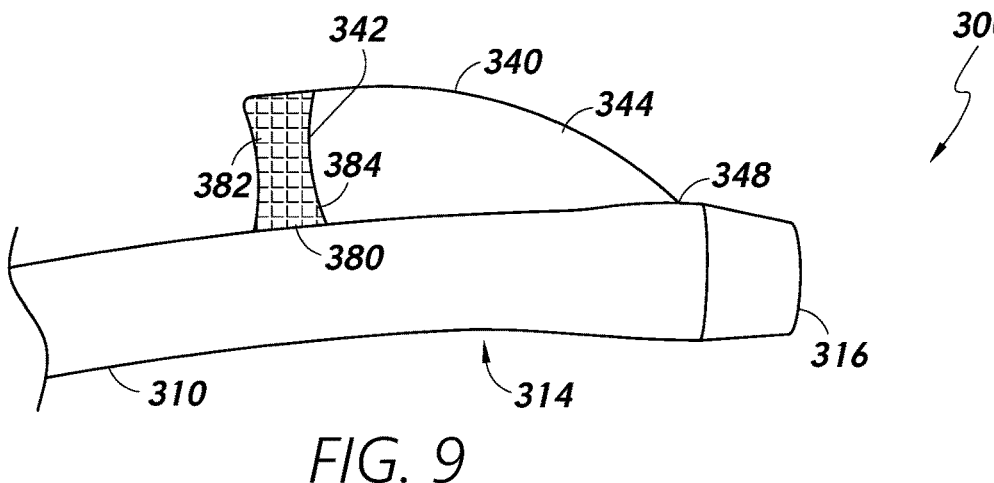
FIG. 9 is a schematic diagram of an example of a steerable sheath comprising a partially circumferential balloon anchor and a deformable panel coupled thereto.

FIG. 9 is a schematic diagram of an example of a steerable sheath 300 comprising a partially circumferential balloon anchor 340 and a deformable panel 380 coupled thereto. The steerable sheath 300 can comprise an elongate tubular member 310. A distal portion 314 of the elongate tubular member 310 can comprise the partially circumferential balloon anchor 340 thereon.

In some embodiments, the partially circumferential balloon anchor 340 can comprise one or more features of the partially circumferential balloon anchor 240 described with reference to FIGS. 6 through 8. For example, the partially circumferential balloon anchor 340 can be inflatable. The partially circumferential balloon anchor 340, when in an inflated state, can be configured to contact and engage with the coronary sinus ostium and a portion of the coronary sinus adjacent to the ostium, so as to facilitate reliable positioning of the elongate tubular member 310 within the coronary sinus. For example, the distal portion 344 of the partially circumferential balloon anchor 340 can comprise a tapered longitudinal profile, the tapered longitudinal profile tapering toward the distal end 348 of the partially circumferential balloon anchor 340. The longitudinal profile can extend along a direction parallel or substantially parallel to a longitudinal axis of the elongate tubular member 310. In some embodiments, the tapered longitudinal profile can comprise a curve, including a convex curve. The distal end 348 of the circumferential balloon anchor 340 can be spaced from or at the distal end 316 of the elongate tubular member 310.

In some embodiments, the partially circumferential balloon anchor 340 can be positioned around less than about 50% of the circumference of the distal portion 314 of the elongate tubular member 310, or less than about 40%, or less than about 30%, or less than about 25%, or less than about 20%.

The proximal portion 342 of the partially circumferential balloon anchor 340 can extend laterally from the distal portion 314 of the elongate tubular member 310. The deformable panel 380 can be coupled to the proximal portion 342. The deformable panel 380 can extend laterally from the distal portion 314, including an example which extends perpendicularly or substantially perpendicularly from the distal portion 314. For example, the deformable panel 380 can comprise a proximal surface 382 and a distal surface 384. The distal surface 384 can be coupled to the proximal portion 342 of the balloon anchor 340. The deformable panel 380 can provide mechanical support, for example providing mechanical reinforcement, for the proximal portion 342. The deformable panel 380 can be configured to reduce deformation of an inflated partially circumferential balloon anchor 340, such as when the partially circumferential balloon anchor 340 engages the coronary sinus ostium and an adjacent portion of the coronary sinus. Reduced deformation of the inflated balloon anchor 340 can provide increased reliability in positioning of the elongate tubular member 310 within the coronary sinus.

Figure 10A:
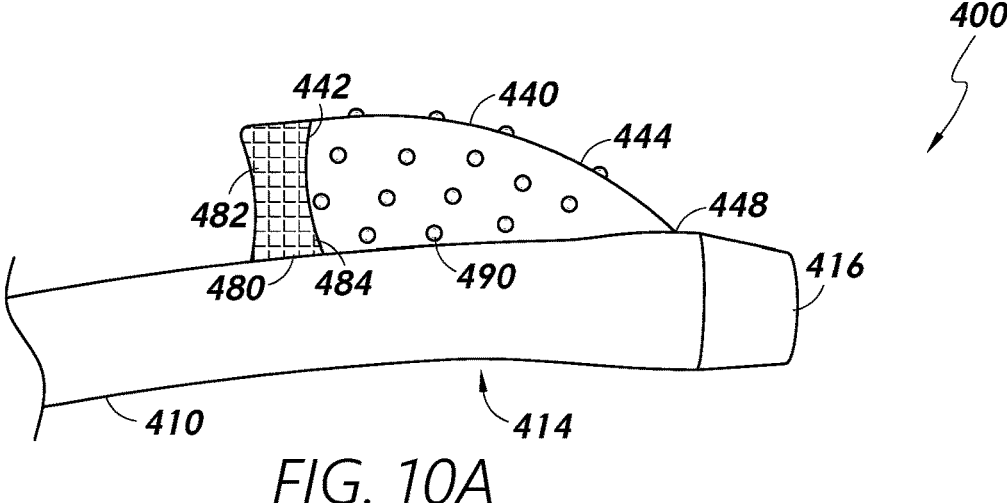
FIGS. 10A and 10B are schematic diagrams of examples of steerable sheaths which comprise a partially circumferential balloon anchor, where the partially circumferential balloon anchor can comprise a textured surface thereon.
Figure 10B:
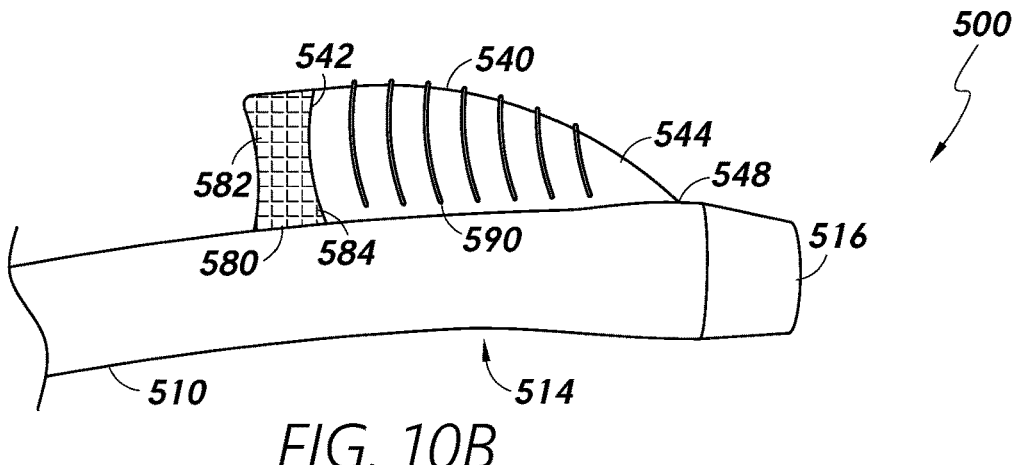

FIGS. 10A and 10B are schematic diagrams of examples of two steerable sheaths each of which includes a partially circumferential balloon anchor comprising a textured surface thereon. FIG. 10A shows an example of a steerable sheath 400 including a partially circumferential balloon anchor 440 which comprises a plurality of bumps 490 on an exterior surface. FIG. 10B shows an example of a steerable sheath 500 including partially circumferential balloon anchor 540 which comprises a plurality of ridges 590 on an exterior surface.

The plurality of bumps 490 and the plurality of ridges 590 can be on a portion or all of the exterior surface of the partially circumferential balloon anchors 440, 540. In some embodiments, the plurality of bumps 490 and the plurality of ridges 590 can be only on the distal portion 444 or the distal portion 544, respectively. The plurality of bumps 490 and the plurality of ridges 590 can facilitate desired engagement of the balloon anchor 440 or the balloon anchor 540, respectively, with the coronary sinus ostium and an adjacent portion of the coronary sinus.

In some embodiments, a partially circumferential balloon anchor can comprise a textured exterior surface configured to engage with the coronary sinus ostium and an adjacent portion of the coronary sinus, the textured exterior surface comprising both a plurality of bumps and a plurality of ridges. It will also be understood that textured surfaces comprising one or more other patterns, in addition or in the alternative, can be applicable.

In some embodiments, the partially circumferential balloon anchors 440, 540 can comprise one or more features of the partially circumferential balloon anchor 340 described with reference to FIG. 9. For example, the partially circumferential balloon anchors 440, 540 can be inflatable. The partially circumferential balloon anchors 440, 540, when in an inflated state, can be configured to contact and engage with the coronary sinus ostium and a portion of the coronary sinus adjacent to the ostium, so as to facilitate reliable positioning of the elongate tubular members 410, 510 within the coronary sinus. The partially circumferential balloon anchors 440, 540 can be positioned on distal portions 414, 514 of the elongate tubular members 410, 510. The distal ends 448, 548 of the circumferential balloon anchors 440, 540 can be spaced from or at the distal ends 416, 516 of the elongate tubular members 410, 510. While inflated, the partially circumferential balloon anchors 440, 540 can comprise a shape to engage the coronary sinus ostium and a portion of the coronary sinus adjacent to the ostium. For example, the distal portions 444, 544 of the partially circumferential balloon anchors 440, 540 can comprise a tapered longitudinal profile, the tapered longitudinal profile tapering toward the distal ends 448, 548 of the partially circumferential balloon anchors 440, 540. The longitudinal profile can extend along a direction parallel or substantially parallel to a longitudinal axis of the elongate tubular members 410, 510. In some embodiments, the tapered longitudinal profile can comprise a curve, including a convex curve. The proximal portions 442, 542 of the partially circumferential balloon anchors 440, 540 can be coupled to deformable panels 480, 580. The deformable panels 480, 580 can comprise respective proximal surfaces 482, 582 and distal surfaces 484, 584. The distal surfaces 484, 584 can be coupled to the proximal portions 442, 542 of the partially circumferential balloon anchors 440, 540.

In some embodiments, the partially circumferential balloon anchors 440, 540 can be positioned around less than about 50% of the circumference of the distal portions 414, 514 of the elongate tubular members 410, 510, or less than about 40%, or less than about 30%, or less than about 25%, or less than about 20%.

Figure 11A:
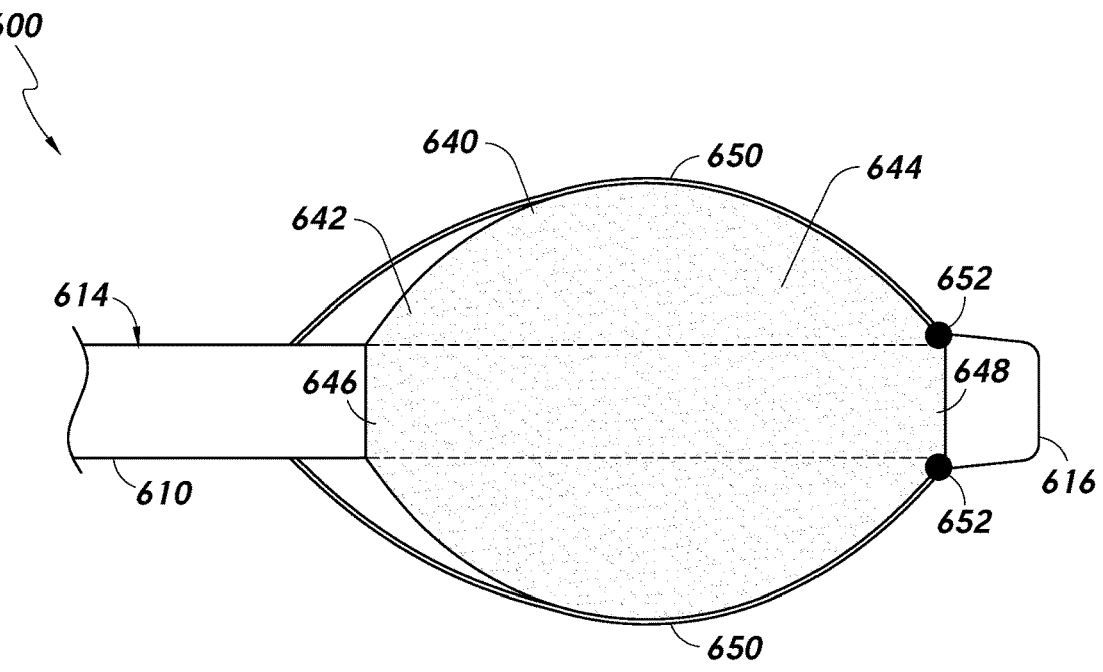
FIGS. 11A and 11B are schematic diagrams showing an example of a steerable sheath which comprises a circumferential balloon anchor and a plurality of cords circumferentially distributed around the circumferential balloon anchor.
Figure 11B:
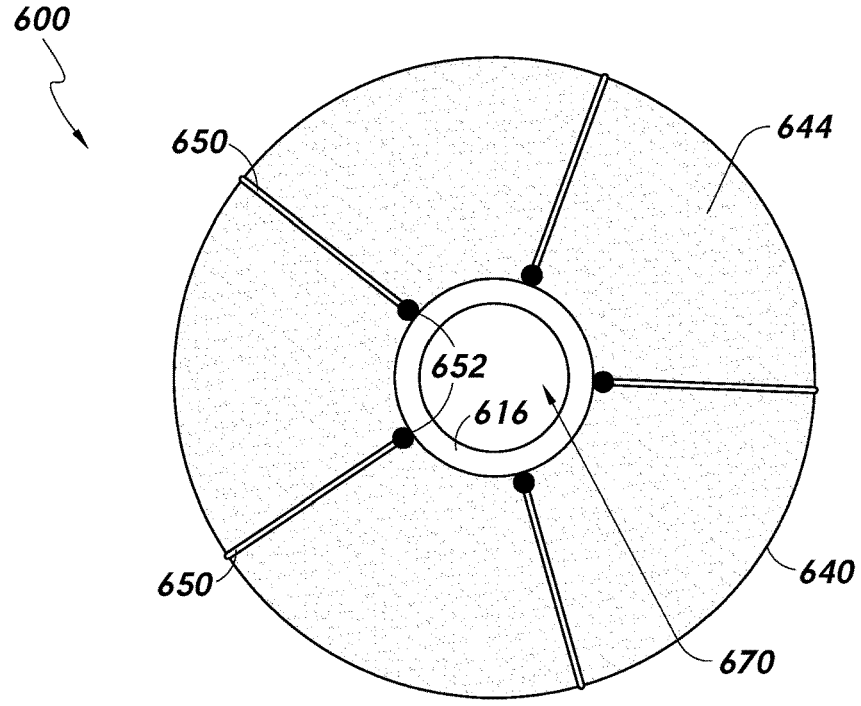
Figure 12A:
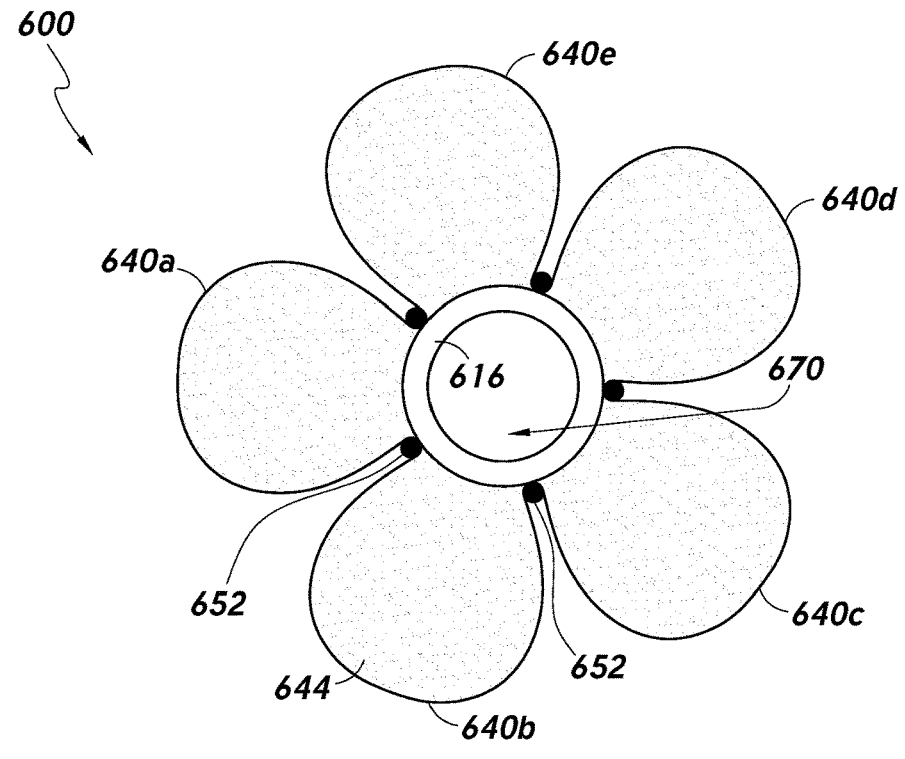
FIGS. 12A and 12B are schematic diagrams showing the plurality of cords engaged with the circumferential balloon anchor of FIGS. 11A and 11B, so as to form corresponding indentations on the circumferential balloon anchor.
Figure 12B:
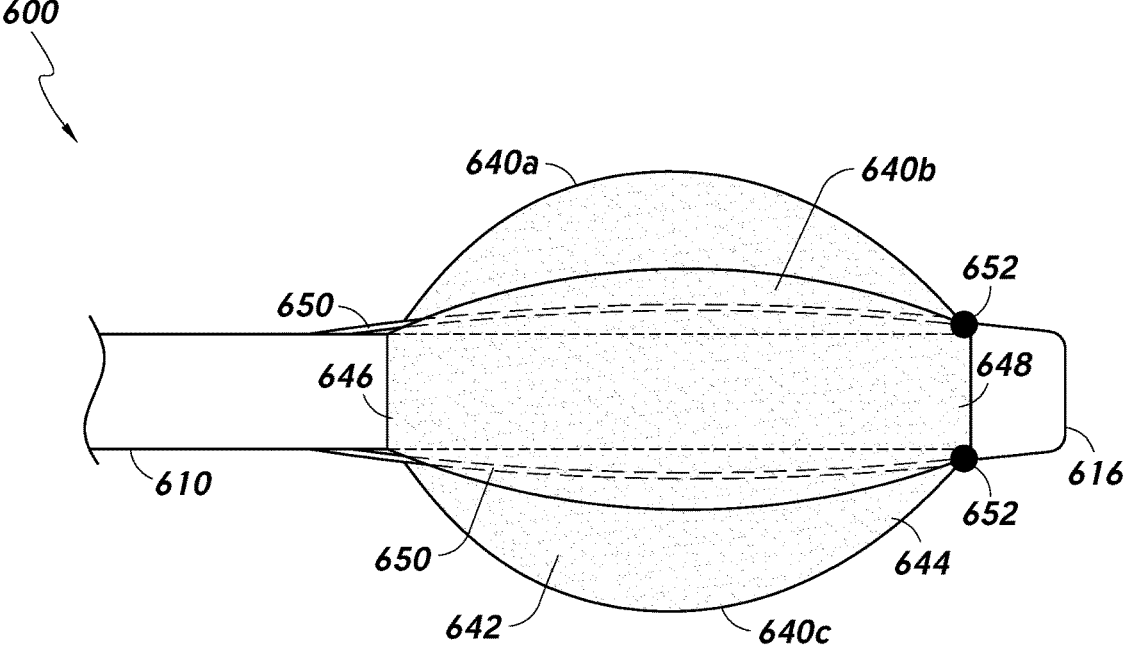

FIGS. 11A and 11B are schematic diagrams showing an example of a steerable sheath 600 comprising a circumferential balloon anchor 640 circumferentially disposed around an elongate tubular member 610 of the steerable sheath 600 and a plurality of cords 650 circumferentially distributed around the circumferential balloon anchor 640. FIGS. 11A and 11B show an inflated circumferential balloon anchor 640. FIG. 11A is a side view of the steerable sheath 600 and FIG. 11B is a view of the steerable sheath 600 from a distal end 616 of the elongate tubular member 610. FIGS. 12A and 12B are schematic diagrams showing the plurality of cords 650 engaged with the inflated circumferential balloon anchor 640 to form the corresponding indentations on the inflated circumferential balloon anchor 640. FIG. 12A is a view of the steerable sheath 600 from the distal end 616 of the elongate tubular member 610. FIG. 12B is a side view of the steerable sheath 600. The elongate tubular member 610 can comprise an inner lumen 670 configured to receive instrumentation for delivering one or more therapy devices to a target location, such as a delivery catheter for carrying an atrial shunt device to a target location on the left atrial wall. The inflated circumferential balloon anchor 640 can be configured to engage with the coronary sinus ostium, or the coronary sinus ostium and an adjacent portion of the coronary sinus, while blood flow is permitted through the ostium. Blood flow through the ostium may be along one or more paths defined at least in part by one or more of the plurality of indentations. As shown in the figures, the circumferential balloon anchor 640 can be a distance from the distal end 616 of the elongate tubular member 610. For example, a distal end 648 of the circumferential balloon anchor 640 can be a distance proximal of the distal end 616 of the elongate tubular member 610. In some embodiments, the circumferential balloon anchor 640 can be at the distal end 616 of the elongate tubular member 610.

Referring to FIG. 11A, the circumferential balloon anchor 640 can be circumferentially positioned around a distal portion 614 of the elongate tubular member 610. Distal ends 652 of each of the plurality of cords 650 can be coupled to respective locations on the distal portion 644 of the circumferential balloon anchor 640. In some embodiments, distal ends 652 of each of the plurality of cords 650 can be coupled to respective locations on the distal portion 614 of the elongate tubular member 610. Each of the plurality of cords 650 can comprise a portion which extends over at least a portion of the circumferential balloon anchor 640, extending along a longitudinal axis of the elongate tubular member 610.

Referring to FIG. 11B, respective distal ends 652 of the plurality of cords 650 can be coupled to corresponding locations on the distal portion 644 of the circumferential balloon anchor 640 and be distributed around the circumferential balloon anchor 640. The circumferential balloon anchor 640 can have a longitudinal axis symmetry, for example being symmetrical around an axis parallel or substantially parallel to the longitudinal axis of the elongate tubular member 610. In some embodiments, the plurality of cords 650 can be evenly or substantially evenly distributed around the circumferential balloon anchor 640, for example dividing the circumferential balloon anchor 640 into even or substantially even portions. FIG. 11B shows five cords 650 positioned around the balloon circumferential anchor 640. For example, the five cords 650 can be evenly or substantially evenly distributed around the circumferential balloon anchor 640 to divide the circumferential balloon anchor into five equal or substantially equal portions. In some embodiments, the plurality of cords 650 may not be evenly distributed around the circumferential balloon anchor 640.

The plurality of cords 650 can engage an inflated circumferential balloon anchor 640 to form corresponding indentations on the inflated circumferential balloon anchor 640. Referring to FIG. 12A, the plurality of indentations can divide the circumferential balloon anchor 640 into a plurality of portions. For example, the five cords 650 can divide the inflated circumferential balloon anchor 640 into five portions 640a, 640b, 640c, 640d, 640e. In some embodiments, the five cords 650 can be evenly or substantially evenly distributed around the balloon anchor 640 such that the five portions 640*a*, 640*b*, 640*c*, 640*d*, 640*e* are uniform or substantially uniform in size and/or shape.

The circumferential balloon anchor 640 can be inflated, and the plurality of cords 650 can be tensioned such that the plurality of cords 650 can compress the inflated circumferential balloon anchor 640 to form the corresponding plurality of indentations. The circumferential balloon anchor 640 can be inflated before and/or after being positioned at the coronary sinus ostium. After the circumferential balloon anchor 640 is in the inflated state, the plurality of cords 650 can be moved proximally relative to the elongate tubular member 610, for example proximally along a longitudinal axis of the elongate tubular member 610, to tension the plurality of cords 650. In some embodiments, the plurality of cords 650 can be in a tensioned state prior to inflation of the circumferential balloon anchor 640 such that inflating the circumferential balloon anchor 640 results in formation of the corresponding plurality of indentations. Pre-tensioning the plurality of cords 650 can reduce needed manipulation of the steerable sheath 600 during a procedure, providing a simplified procedure.

In some embodiments, the circumferential balloon anchor 640 can be configured to engage the ostium of the coronary sinus. In some embodiments, the circumferential balloon anchor 640 can be configured to engage the ostium and an adjacent portion of the coronary sinus. Referring to FIG. 12B, in some embodiments, the distal portion 644 of the circumferential balloon anchor 640 can have a longitudinal profile comprising a taper toward the distal end 648 of the circumferential balloon anchor 640, the longitudinal profile extending along a direction parallel or substantially parallel to the longitudinal axis of the elongate tubular member 610. The taper of the longitudinal profile can be configured to facilitate desired engagement of the distal portion 644 with the coronary sinus ostium and/or the portion of the coronary sinus adjacent to the ostium. In some embodiments, the tapered distal portion 644 can comprise a curvature, such as a convex curvature. In some embodiments, a proximal portion 642 of the circumferential balloon anchor 640 can comprise a taper to facilitate movement of the circumferential balloon anchor 640, including retraction of the circumferential balloon anchor 640. The longitudinal profile of the proximal portion 642 can comprise a curved taper, such as a curved convex taper, which tapers towards the proximal end 646 of the circumferential balloon anchor 640. In some embodiments, the circumferential balloon anchor 640 can have a maximum cross-sectional size at or around a mid-portion of the anchor 640, and a longitudinal profile of both the proximal portion 642 and distal portion 644 comprising a taper, including a curved convex taper, from or around the mid-portion of the anchor 640 toward the proximal end 646 and the distal tend 648, respectively.

In some embodiments, a circumferential balloon anchor can comprise a textured exterior surface configured to engage with the coronary sinus ostium, or the coronary sinus ostium and an adjacent portion of the coronary sinus. The textured exterior surface can comprise one or both of a plurality of bumps and a plurality of ridges. It will be understood that textured surfaces comprising one or more other patterns, in addition or in the alternative, can be applicable.

Figure 13A:
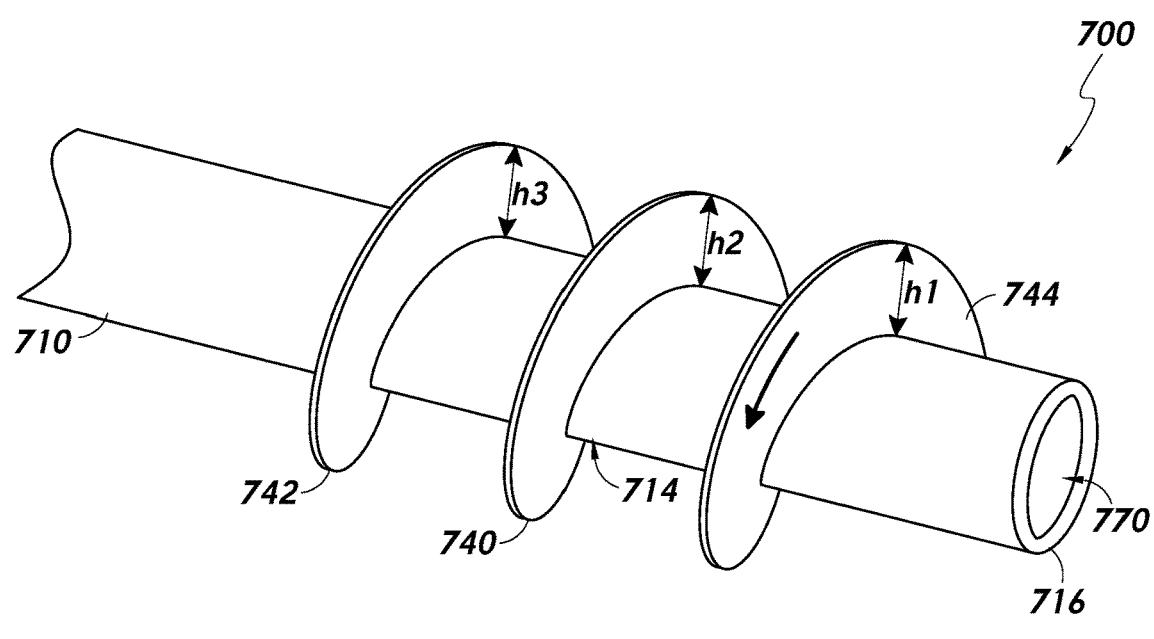
FIGS. 13A and 13B are schematic diagrams showing examples of steerable sheaths comprising a helical rib anchor.
Figure 13B:
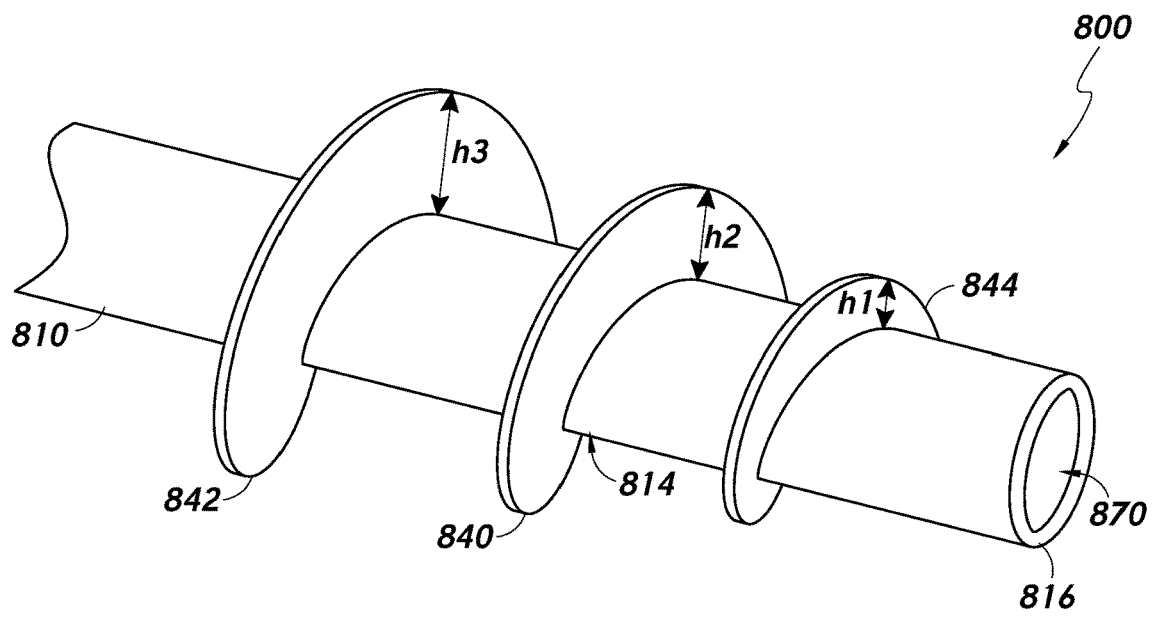

FIGS. 13A and 13B show examples of steerable sheaths comprising helical rib anchors. FIG. 13A is a perspective view of an example of a steerable sheath 700 comprising a helical rib anchor 740 disposed around a distal portion 714 of an elongate tubular member 710. FIG. 13B is a perspective view of another example of a steerable sheath 800 comprising a helical rib anchor 840 disposed around a distal portion 814 of an elongate tubular member 810. The helical rib anchors 740, 840 can be configured to engage with the coronary sinus ostium and a portion of the coronary sinus adjacent to the ostium. In some embodiments, the helical rib anchors 740, 840 can be deformable to facilitate insertion and/or retraction, and/or secure engagement with the coronary sinus ostium and an adjacent portion of the coronary sinus. The helical rib anchors 740, 840 can be a distance from or at respective distal ends 716, 816 of the elongate tubular members 710, 810 (e.g., distal ends 744, 844 of the helical rib anchors 740, 840 can be a distance from or at respective distal ends 716, 816 of the elongate tubular members 710, 810). The elongate tubular members 710, 810 can comprise respective inner lumens 770, 870 configured to receive instrumentation for delivering one or more therapy devices to a target location, such as a delivery catheter for carrying an atrial shunt device to a target location on the left atrial wall.

At least a portion of the helical anchors 740, 840 can be configured to be positioned within the coronary sinus. In some embodiments, one or both of the helical rib anchors 740, 840 can be configured to be entirely or substantially entirely positioned within the coronary sinus, both the distal ends 744, 844 and proximal ends 742, 842 being configured to be positioned within the coronary sinus. For example, the proximal ends 742, 842 can be configured to engage with the ostium. In some embodiments, one or both of the helical rib anchors 740, 840 can be configured to be only partially positioned within the coronary sinus. For example, the distal ends 744, 844 and not the proximal ends 742, 842 can be configured to be positioned within the coronary sinus. In some embodiments, an extent to which the helical rib anchors 740, 840 can be positioned into a coronary sinus can be based on individual anatomy.

The helical rib anchors 740, 840 can be configured to allow blood flow through the coronary sinus ostium while the helical rib anchors 740, 840 are in their respective target positions. Blood can flow along a path defined at least in part by the helical rib anchors 740, 840. For example, blood can flow along the helical ribs, such as shown by the arrows in FIGS. 13A and 13B. While the helical rib anchors 740, 840 are positioned at their respective target locations, blood can flow along a path defined at least in part by the helical ribs of the helical anchors 740, 840 through the coronary sinus ostium.

Referring to FIG. 13A, a height at which the helical rib anchor 740 extends from the elongate tubular member 710 can be uniform or substantially uniform along a dimension parallel or substantially parallel to a longitudinal axis of the elongate tubular member 710. For example, a first height, h1, a second height, h2, and a third height, h3, of the helical rib anchor 740 shown in FIG. 13A can be the same or substantially the same.

Referring to FIG. 13B, a height at which the helical rib anchor 840 extends from the elongate tubular member 810 can increase along a dimension parallel or substantially parallel to a longitudinal axis of the elongate tubular member 810, for example increasing with increased distance from the distal end 816 of the elongate tubular member 810. In FIG. 13B, a first height, h1, of the helical rib anchor 840 can be smaller than a second height, h2, which can be smaller than a third height, h3. In some embodiments, a decreasing height of the helical rib anchor 840 toward the distal end 816 of the elongate tubular member 810 can be configured to provide improved engagement with the coronary sinus ostium and an adjacent portion of the coronary sinus, such as by conforming to the anatomy of the coronary sinus.

Figure 14A:
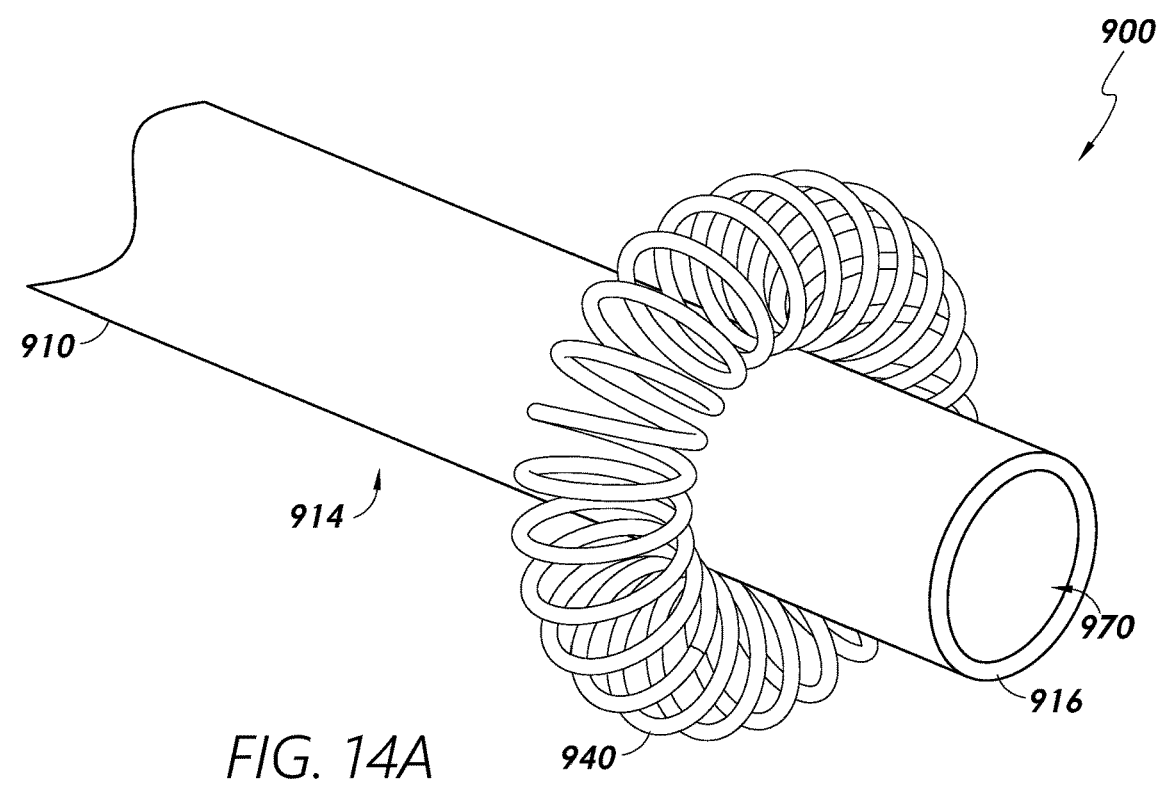
FIGS. 14A and 14B are schematic diagrams showing examples of steerable sheaths comprising one coil anchor and two coil anchors, respectively.
Figure 14B:
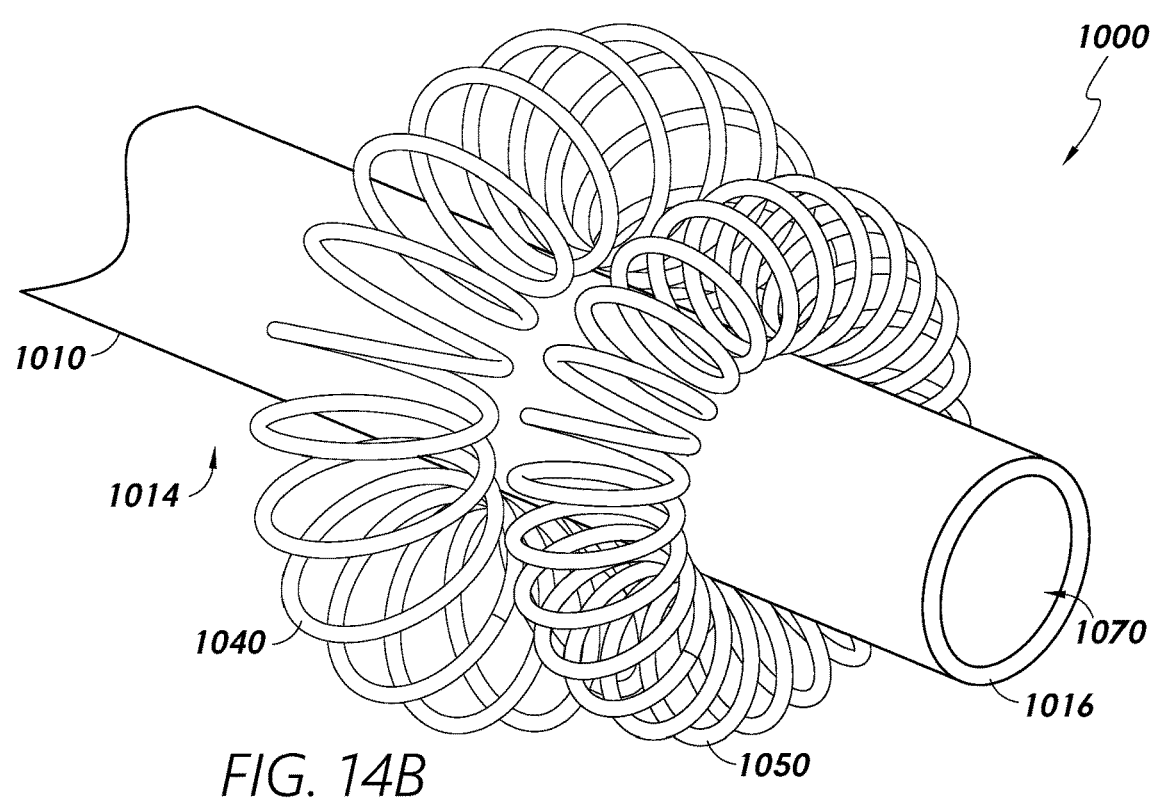

FIGS. 14A and 14B show examples of steerable sheaths comprising one or more coil anchors. FIG. 14A is a perspective view of an example of a steerable sheath 900 comprising a coil anchor 940 disposed around a distal portion 914 of an elongate tubular member 910. FIG. 14B is a perspective view of an example of a steerable sheath 1000 comprising a first coil anchor 1040 and a second coil anchor 1050 disposed around a distal portion 1014 of an elongate tubular member 1010. Each of the elongate tubular members 910, 1010 can comprise an inner lumen 970, 1070 configured to receive instrumentation for delivering one or more therapy devices to a target location. For example, the inner lumens 970, 1070 can be configured to receive a delivery catheter for carrying an atrial shunt device to a target location on the left atrial wall.

The coil anchor 940 of the steerable sheath 900 can be configured to engage with the coronary sinus ostium. The coil anchor 940 can be positioned at the ostium while a distal end 916 of the elongate tubular member 910 can be at or proximate to a target tissue site on the left atrial wall accessible from within the coronary sinus. For example, the coil anchor 940 can be at a distance from the distal end 916 of the elongate tubular member 910 such that the distal end 916 can be positioned into the coronary sinus while at least a portion of the coil anchor 940 is in the ostium. In some embodiments, the coil anchor 940 can be positioned to engage the ostium such that a portion of the coil anchor 940 is in the right atrium and a portion of the coil anchor 940 is in the coronary sinus. The coil anchor 940 can be configured to permit blood to flow through the ostium while the coil anchor 940 is in desired engagement with the ostium. For example, blood can flow between the coils of the coil anchor 940.

Referring to FIG. 14B, the first coil anchor 1040 of the steerable sheath 1000 can be positioned adjacent to and proximal of second coil anchor 1050 on the distal portion 1014 of the elongate tubular member 1010. The second coil anchor 1050 can include coils comprising a diameter smaller than that of the first coil anchor 1040. The first coil anchor 1040 can be configured to engage the coronary sinus ostium and the second coil anchor 1050 can be configured to engage a portion of the coronary sinus adjacent to the ostium. For example, the first coil anchor 1040 and the second coil anchor 1050 can be at a distance from the distal end 1016 of the elongate tubular member 1010 such that the distal end 1016 can be positioned within the coronary sinus while the first coil anchor 1040 and the second coil anchor 1050 engage the coronary sinus ostium and an adjacent portion of the coronary sinus, respectively. In some embodiments, the second coil anchor 1050 can be at the distal end 1016 of the elongate tubular member 1010.

The coil anchors 1040, 1050 can be configured to permit blood to flow through the ostium while the coil anchors 1040, 1050 are in desired engagement with the coronary sinus ostium and an adjacent portion of the coronary sinus. For example, blood can flow through the ostium between coils of the coil anchors 1040, 1050.

In some embodiments, one or more of the coil anchors 940, 1040, 1050 can be expandable. One or more of the coil anchors 940, 1040, 1050 can be kept in a compact state during at least a part of the insertion of the elongate tubular members 910, 1010 to the target tissue site. In some embodiments, one or more of the coil anchors 940, 1040, 1050 can comprise shape memory material. The one or more coil anchors 940, 1040, 1050 can be maintained in the compact state until a predetermined location is reached. The one or more coil anchors 940, 1040, 1050 can then be allowed to assume an expanded state, such as when the one or more coil anchors 940, 1040, 1050 comprising the shape memory material can assume their respective desired coil configurations. In some embodiments, a diameter of the coils of one or more of the coil anchors 940, 1040, 1050 can be adjusted based on patient anatomy. For example, a degree of expansion of the one or more coil anchors 940, 1040, 1050 can be adjusted during an implantation procedure in response to a size of a coronary sinus ostium, and/or an adjacent portion of the coronary sinus.

In some embodiments, the one or more of the coil anchors 940, 1040, 1050 can assume an expanded state after the coil anchors 940, 1040, 1050 are positioned at respective target locations. For example, after the distal ends 916, 1016 of the elongate tubular members 910, 1010 are positioned at or adjacent to the target tissue site, one or more of the coil anchors 940, 1040, 1050 can assume the expanded state. In some embodiments, the one or more of the coil anchors 940, 1040, 1050 can be expanded until desired engagement with the coronary sinus ostium and/or an adjacent portion of the coronary sinus is achieved. In some embodiments, one or more of the coil anchors 940, 1040, 1050 can assume an expanded state before the coil anchors 940, 1040, 1050 are positioned at respective target locations. For example, the one or more of the coil anchors 940, 1040, 1050 can be expanded after the one or more of the coil anchors 940, 1040, 1050 are extended from the inferior vena cava or the superior vena cava into the right atrium but before the one or more of the coil anchors 940, 1040, 1050 are positioned at their respective desired locations. In some embodiments, the one or more of the coil anchors 940, 1040, 1050 can be expanded both before and after the coil anchors 940, 1040, 1050 are positioned at respective target locations. For example, the one or more of the coil anchors 940, 1040, 1050 can assume a partially expanded state before being positioned at the respective desired locations, such as while the one or more of the coil anchors 940, 1040, 1050 are in the right atrium. The coil anchors 940, 1040, 1050 can then assume a fully expanded state after the one or more of the coil anchors 940, 1040, 1050 are positioned at their respective desired locations.

Figure 15:
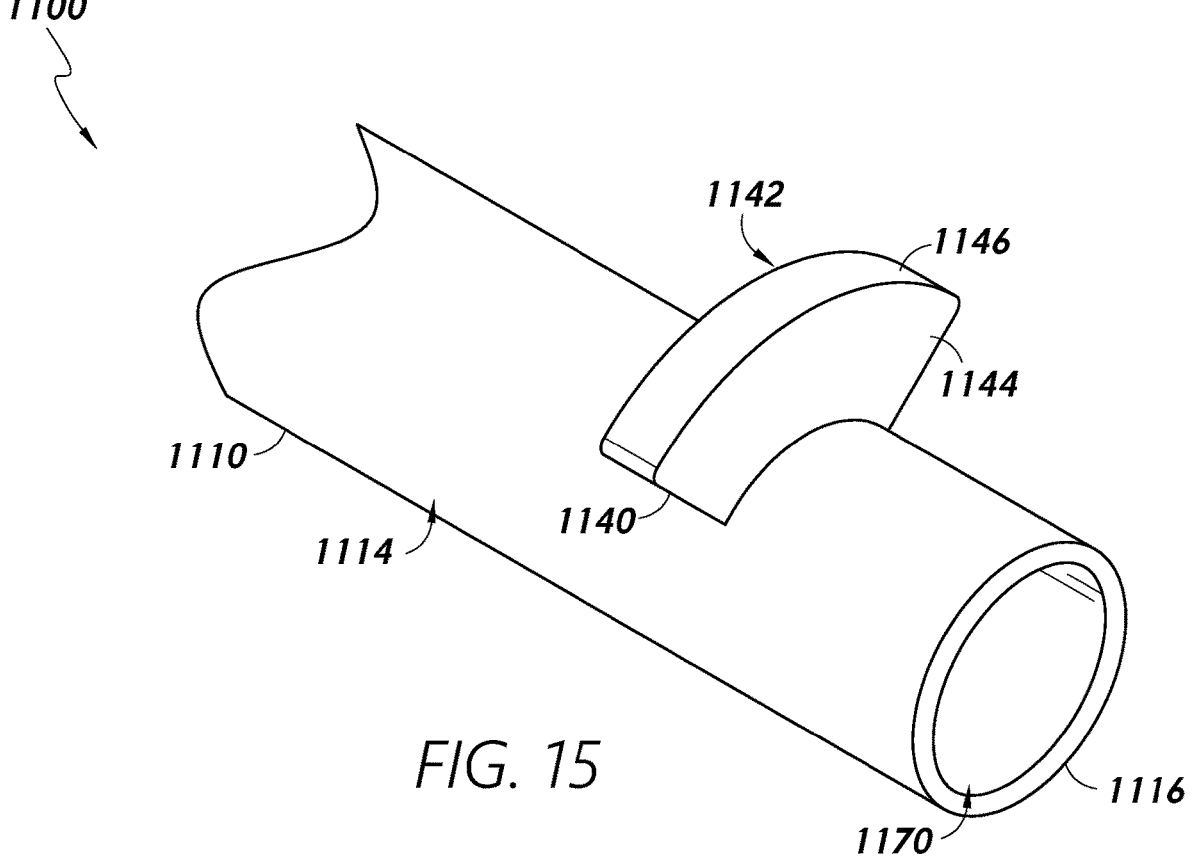
FIG. 15 is a schematic diagram showing an example of a steerable sheath comprising a partially circumferential ring anchor.

FIG. 15 is a perspective view of an example of a steerable sheath 1100 comprising a partially circumferential ring anchor 1140 positioned on an elongate tubular member 1110 of the steerable sheath 1100. The elongate tubular member 1110 can comprise an inner lumen 1170 configured to receive instrumentation for delivering one or more therapy devices to a target location, such as a delivery catheter for carrying an atrial shunt device to a target location on the left atrial wall. The partially circumferential ring anchor 1140 can be positioned on a distal portion 1114 of the elongate tubular member 1110. The partially circumferential ring anchor 1140 can be configured to be positioned to engage with the coronary sinus ostium. The partially circumferential ring anchor 1140 can be a distance from or at the distal end 1116 of the elongate tubular member 1110 (e.g., a distal portion 1144 of the partially circumferential ring anchor 1140 can be a distance from or at the distal end 1116 of the elongate tubular member 1110).

As shown in FIG. 15, the partially circumferential ring anchor 1140 can be positioned around only a portion of the circumference of the distal portion 1114. As used herein, a "partially circumferential ring anchor" can refer to any ring anchor configured to be positioned on, disposed around and/or extending from, any partial portion of the circumference of the distal portion 1114, and where the ring anchor does not circumscribe the distal portion 1114.

The partially circumferential ring anchor 1140 can facilitate blood flow through the coronary sinus ostium and past the partially circumferential ring anchor 1140 while the partially circumferential ring anchor 1140 is positioned at and in engagement with the coronary sinus ostium, or the coronary sinus ostium and a portion of the coronary sinus adjacent to the ostium. The partially circumferential ring anchor 1140 can provide desired contact with the coronary sinus ostium, or the coronary sinus ostium and a portion of the coronary sinus adjacent to the ostium, to provide stable positioning of the elongate tubular member 1110, while allowing sufficient area around the steerable sheath 1100 at the coronary sinus ostium such that sufficient blood flow can pass therethrough. In some embodiments, the partially circumferential ring anchor 1140 can be positioned around less than about 50% of the circumference of the distal portion 1114 of the elongate tubular member 1110, or less than about 40%, less than about 30%, less than about 25%, or less than about 20%.

The partially circumferential ring anchor 1140 can have a proximal portion 1142, a distal portion 1144 and a lateral portion 1146 extending between the proximal portion 1142 and the distal portion 1144. In some embodiments, the distal portion 1144 and/or the lateral portion 1146 can be configured to engage with the coronary sinus ostium, or both the coronary sinus ostium and a portion of the coronary sinus adjacent to the ostium. In some embodiments, at least a portion of the lateral portion 1146 can be configured to engage the ostium, or the ostium and a portion of the coronary sinus adjacent to the ostium. For example, the partially circumferential ring anchor 1140 can be sized such that when at least a portion of the anchor 1140 is positioned within the coronary sinus ostium, the lateral portion 1146 can be configured to engage the coronary sinus ostium, or the coronary sinus ostium and an adjacent portion, to provide stable positioning of the elongate tubular member 1110.

In some embodiments, the distal portion 1144 can be configured to engage the ostium. In some embodiments, the partially circumferential ring anchor 1140 can be positioned against the ostium such that the distal portion 1144 is configured to engage the ostium. For example, the partially circumferential ring anchor 1140 can be positioned against the coronary sinus ostium such that the proximal portion 1142 and the lateral portion 1146 of the partially circumferential ring anchor 1140 are outside or substantially outside of the coronary sinus, and the distal portion 1144 can engage the coronary sinus ostium.

In some embodiments, a partially circumferential ring anchor can comprise a planar or substantially planar distal portion and/or proximal portion. In some embodiments, the distal portion and/or the proximal portion can be non-planar. In some embodiments, a distal portion of a partially circumferential ring anchor can comprise a shape and/or dimension to engage the coronary sinus ostium, or the coronary sinus ostium and an adjacent portion of the coronary sinus ostium. For example, the distal portion can have a longitudinal profile comprising a taper toward a distal end of the partially circumferential ring anchor. The longitudinal profile can extend along a direction parallel or substantially parallel to a longitudinal axis of the elongate tubular member. The tapered longitudinal profile may comprise a curved taper, such as a convex taper, configured to engage the coronary sinus ostium and an adjacent portion of the coronary sinus. In some embodiments, the lateral portion can be configured to engage the coronary sinus ostium and the distal portion can be configured to engage a portion of the coronary sinus adjacent to the ostium.

In some embodiments, a steerable sheath can comprise a suction anchor. The steerable sheath can comprise an elongate tubular member, and the suction anchor can be positioned on a distal portion of the elongate tubular member. The suction anchor can be configured to engage with the coronary sinus ostium, or the coronary sinus ostium and an adjacent portion, and permit blood to flow through the ostium, while the suction anchor is positioned at the ostium.

FIG. 16 is a flow diagram of an example of a procedure 1600 for deploying a steerable sheath into the coronary sinus. The steerable sheath can comprise an elongate tubular member and an anchor positioned on a distal portion of the elongate tubular member. The steerable sheath can have one or more configurations as described herein. For example, the anchor can comprise any one of the partially circumferential balloon anchor, circumferential balloon anchor, helical rib anchor, coil anchor, partially circumferential ring anchor, and suction anchor, as described herein.

In block 1602, the procedure 1600 involves providing the steerable sheath. In block 1604, the procedure 1600 involves introducing the distal portion of the elongate tubular member through the inferior vena cava or superior vena cava, and into the right atrium. In some embodiments, the elongate tubular member can be introduced through a femoral vein and into the inferior vena cava. In some embodiments, the elongate tubular member can be introduced through a jugular vein or a subclavian vein and into the superior vena cava. In block 1606, the procedure 1600 involves inserting the distal end of the elongate tubular member into the coronary sinus from the right atrium via the coronary sinus ostium, and the anchor can be positioned at the coronary sinus ostium. The anchor can be on the distal portion of the elongate tubular member and at a distance from a distal end of the elongate tubular member. The anchor can be spaced from the distal end of the elongate tubular member such that while the distal end is placed at or adjacent to a target tissue site, the anchor can be positioned to engage with the coronary sinus ostium. In some embodiments, the anchor can be at the distal end of the elongate tubular member.

In block 1608, the procedure 1600 involves engaging the anchor with the coronary sinus ostium, while blood flow is permitted through the ostium past the anchor. In some embodiments, the anchor can be engaged with both the coronary sinus ostium and a portion of the coronary sinus adjacent to the ostium.

FIG. 17 is a flow diagram of an example of a procedure 1700 for deploying a steerable sheath comprising a circumferential balloon anchor into the coronary sinus. The steerable sheath can comprise an elongate tubular member and a circumferential balloon anchor positioned on a distal portion of the elongate tubular member. A plurality of cords can be circumferentially distributed around the circumferential balloon anchor. Respective distal ends of the plurality of cords can be coupled to corresponding locations on a distal portion of the circumferential balloon anchor. In some embodiments, respective distal ends of the plurality of cords can be coupled to corresponding locations on the distal portion of the elongate tubular member. In block 1702, the procedure 1700 involves providing the steerable sheath. In block 1704, the procedure 1700 involves introducing the distal portion of the elongate tubular member through the inferior vena cava or superior vena cava and into the right atrium. The circumferential balloon anchor can be on the distal portion of the elongate tubular member at a distance away from a distal end of the elongate tubular member. In some embodiments, the circumferential balloon anchor can be at the distal end of the elongate tubular member. In block 1706, the procedure 1700 involves inserting the distal end of the elongate tubular member into the coronary sinus from the right atrium via the coronary sinus ostium, and the circumferential balloon anchor can be positioned at the coronary sinus ostium.

In block 1708, the procedure 1700 involves inflating the circumferential balloon anchor to engage the circumferential balloon anchor with the plurality of cords to create a plurality of corresponding circumferentially distributed indentations around the inflated circumferential balloon anchor. The plurality of cords can be tensioned such that the plurality of cords can engage the inflated circumferential balloon anchor to provide the corresponding circumferentially distributed indentations. For example, the plurality of cords can be moved proximally in a direction along a longitudinal axis of the elongate tubular member to tension the plurality of cords such that the plurality of cords compress the inflated circumferential balloon anchor. The plurality of indentations can be formed by compression of the inflated circumferential balloon anchor using the plurality of cords.

The circumferential balloon anchor can be inflated both before and/or after the distal portion of the elongate tubular member is positioned at a desired location. The circumferential balloon anchor can be kept in a deflated state during at least a part its insertion to the coronary sinus ostium. In some embodiments, the circumferential balloon anchor can be inflated after being positioned at the coronary sinus ostium. The circumferential balloon anchor can be inflated until desired engagement with the coronary sinus ostium, or the coronary sinus ostium and an adjacent portion of the coronary sinus, is achieved. In some embodiments, the circumferential balloon anchor can be inflated after the circumferential balloon anchor is inserted into the right atrium but before the circumferential balloon anchor is positioned at the coronary sinus ostium. In some embodiments, a degree of inflation of the circumferential balloon anchor can be adjusted in response to individual anatomy.

In block 1710, the procedure 1700 involves engaging the inflated circumferential balloon anchor with the coronary sinus ostium, while blood flow is permitted through the ostium along the plurality of indentations. In some embodiments, the circumferential balloon anchor can be engaged with both the coronary sinus ostium and a portion of the coronary sinus adjacent to the ostium. In some embodiments, the circumferential balloon anchor can be deflated for retraction after the medical implant device and/or therapeutic procedure has been delivered.

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A method of accessing a heart location, the method comprising:

providing a steerable sheath comprising an elongate tubular member, a circumferential balloon anchor circumferentially positioned around a distal portion of the elongate tubular member and a plurality of cords circumferentially distributed around the circumferential balloon anchor longitudinally, the plurality of cords being movable relative to the elongate tubular member along a longitudinal axis of the elongate tubular member;

introducing the distal portion of the elongate tubular member through an inferior vena cava or a superior vena cava, and into a right atrium;

inserting a distal end of the elongate tubular member through an ostium of a coronary sinus into the coronary sinus from the right atrium, and positioning the distal end at a target location within the coronary sinus;

inflating the circumferential balloon anchor and moving the plurality of cords proximally relative to the elongate tubular member to tension the plurality of cords to engage an inflated circumferential balloon anchor with the plurality of cords to create corresponding circumferentially distributed longitudinal indentations on the inflated circumferential balloon anchor; and positioning the inflated circumferential balloon anchor partially in the coronary sinus and engaging a distal portion of the inflated circumferential balloon anchor having a longitudinal taper with the ostium of the coronary sinus while permitting blood flow through the ostium past the inflated circumferential balloon anchor along a path defined at least in part by the circumferentially distributed longitudinal indentations.

2. The method of claim 1, wherein respective distal ends of the plurality of cords are coupled to corresponding locations on a distal balloon portion, and wherein moving the plurality of cords longitudinally compresses the inflated circumferential balloon anchor to provide the corresponding circumferentially distributed indentations on the inflated circumferential balloon anchor.

3. The method of claim 1, further comprising inserting into an inner lumen of the elongate tubular member a delivery catheter carrying a therapy device, and advancing a distal end of the delivery catheter from the distal end of the elongate tubular member for positioning at the target location.

4. The method of claim 3, wherein inserting into the inner lumen of the elongate tubular member a delivery catheter carrying a therapy device comprises inserting a shunt delivery catheter carrying an atrial shunt device.

5. The method of claim 1, wherein engaging the distal portion of the inflated circumferential balloon anchor having the longitudinal taper with the ostium comprises engaging a curved convex taper of the distal portion with the ostium.

6. The method of claim 1, further comprising longitudinally dividing the circumferential balloon anchor into a plurality of portions equal to a quantity of the plurality of cords, such that the plurality of portions have a uniform size and shape, based on moving the plurality of cords to tension the plurality of cords.

7. The method of claim 1, wherein the circumferential balloon anchor has a proximal balloon portion and a distal balloon portion, with each portion having a tapered longitudinal profile including a curved convex taper, from a mid-portion of the circumferential balloon anchor toward a proximal end and a distal end of the circumferential balloon anchor, respectively.

8. The method of claim 1, wherein the circumferential balloon anchor has a maximum cross-sectional size at a mid-portion of the circumferential balloon anchor.

9. A method of accessing a heart location, the method comprising:

providing a steerable sheath comprising an elongate tubular member and an anchor positioned on a distal portion of the elongate tubular member, a plurality of cords circumferentially distributed around the anchor longitudinally to the anchor, the plurality of cords being movable relative to the elongate tubular member along a longitudinal axis of the elongate tubular member;

providing a delivery catheter sized for advancement through an inner lumen of the elongate tubular member, the delivery catheter carrying a shunt;

advancing the distal portion of the elongate tubular member through an inferior vena cava or a superior vena cava, and into a right atrium;

inserting a distal end of the elongate tubular member through an ostium of a coronary sinus into the coronary sinus from the right atrium;

expanding the anchor and moving the plurality of cords proximally relative to the elongate tubular member and the anchor to tension the plurality of cords onto the expanded anchor, engaging the expanded anchor to form corresponding longitudinal indentations on the expanded anchor;

engaging a distal portion of the anchor with the ostium of the coronary sinus, the anchor being formed with the longitudinal indentations for permitting blood flow through the ostium past the anchor;

advancing a distal portion of the delivery catheter out of the distal end of the elongate tubular member to deploy the shunt; and deploying the shunt through a wall of the coronary sinus to allow blood to pass from a left atrium into the coronary sinus and alleviate elevated left atrial pressure, wherein engagement of the anchor with the ostium stabilizes the delivery catheter during deployment of the shunt.

10. The method of claim 9, further comprising inserting into the inner lumen of the elongate tubular member the delivery catheter carrying the shunt.

11. The method of claim 9, wherein expanding the anchor and engaging the distal portion of the anchor with the ostium of the coronary sinus comprises positioning the anchor partially within the coronary sinus and engaging a curved convex taper of the distal portion with the ostium.

12. A method of accessing a heart location, the method comprising:

providing a steerable sheath comprising an elongate tubular member, an inflatable balloon anchor on a distal portion of the elongate tubular member, a plurality of cords circumferentially distributed around the inflatable balloon anchor longitudinally, the plurality of cords being movable relative to the elongate tubular member along a longitudinal axis of the elongate tubular member, and a distal portion of the inflatable balloon anchor having a longitudinal profile comprising a taper toward a distal end of the inflatable balloon anchor;

inserting a distal end of the elongate tubular member through an ostium of a coronary sinus into the coronary sinus from the right atrium; and positioning the inflatable balloon partially in the coronary sinus and engaging the distal portion of the inflatable balloon anchor having the taper with the coronary sinus ostium while permitting blood flow through the ostium past the inflatable balloon anchor.

13. The method of claim 12, wherein engaging the inflatable balloon anchor with the coronary sinus ostium comprises inflating the inflatable balloon anchor to engage the inflatable balloon anchor with the coronary sinus ostium.

14. The method of claim 12, wherein providing the inflatable balloon anchor comprises providing a circumferentially disposed inflatable balloon anchor, the method further comprising compressing the circumferentially disposed inflatable balloon anchor along a longitudinal axis of the elongate tubular member to form a plurality of circumferentially distributed indentations on the inflatable balloon anchor.

15. The method of claim 14, wherein compressing the inflatable balloon anchor comprises tensioning the plurality of cords to engage the inflatable circumferential balloon anchor in an inflated state.

16. The method of claim 15, further comprising moving the plurality of cords proximally relative to the elongate tubular member to tension the plurality of cords to engage the inflated circumferential balloon anchor with the plurality of cords to form the circumferentially distributed longitudinal indentations on the inflatable circumferential balloon anchor, and dividing the inflated circumferential balloon anchor into a quantity of portions equal to a quantity of the longitudinal indentations.

17. The method of claim 12, wherein providing the inflatable balloon anchor comprises providing an inflatable balloon anchor comprising a curved convex taper tapering towards a distal end of the inflatable balloon anchor.

18. The method of claim 17, wherein providing the inflatable balloon anchor comprises providing an inflatable balloon anchor comprising a curved convex taper tapering towards a proximal end of the inflatable balloon anchor from a mid-portion of the inflatable balloon anchor.

19. The method of claim 12, further comprising deploying a shunt through a wall of the coronary sinus, via the elongate tubular member, to allow blood to pass from a left atrium into the coronary sinus and alleviate elevated left atrial pressure.

20. The method of claim 12, further comprising providing the inflatable balloon anchor to have a shape and a size to engage with the ostium of the coronary sinus and a portion of the coronary sinus without occluding the ostium of the coronary sinus, thereby permitting blood flow through the ostium of the coronary sinus past the inflatable balloon anchor.

\* \* \* \* \*